US008475810B2

(12) United States Patent
Vindurampulle et al.

(10) Patent No.: US 8,475,810 B2
(45) Date of Patent: Jul. 2, 2013

(54) **ATTENUATED *SALMONELLA ENTERICA* SEROVAR PARATYPHI A AND USES THEREOF**

(75) Inventors: Christofer Vindurampulle, Thornbury (AU); Eileen M. Barry, Ellicott City, MD (US); Myron M. Levine, Columbia, MD (US)

(73) Assignee: University of Maryland, Baltimore, Baltimore, MD (US)

(*) Notice: Subject to any disclaimer, the term of this patent is extended or adjusted under 35 U.S.C. 154(b) by 471 days.

(21) Appl. No.: 12/091,929

(22) PCT Filed: Oct. 30, 2006

(86) PCT No.: PCT/US2006/042148
§ 371 (c)(1), (2), (4) Date: Apr. 28, 2008

(87) PCT Pub. No.: WO2007/053489
PCT Pub. Date: May 10, 2007

(65) Prior Publication Data

US 2008/0233094 A1 Sep. 25, 2008

Related U.S. Application Data

(60) Provisional application No. 60/731,349, filed on Oct. 28, 2005.

(51) Int. Cl.
*A61K 39/112* (2006.01)
*A61K 35/74* (2006.01)

(52) U.S. Cl.
USPC .................. 424/258.1; 424/93.48; 424/235.1

(58) Field of Classification Search
None
See application file for complete search history.

(56) References Cited

U.S. PATENT DOCUMENTS

| | | | |
|---|---|---|---|
| 6,130,082 | A | 10/2000 | Majarian et al. |
| 6,190,669 | B1 | 2/2001 | Noriega et al. |
| 6,703,233 | B1 | 3/2004 | Galen et al. |
| 2005/0180985 | A9 | 8/2005 | Vladoianu |
| 2007/0281348 | A1 | 12/2007 | Galen et al. |
| 2009/0028889 | A1 | 1/2009 | Nakaar et al. |

FOREIGN PATENT DOCUMENTS

| | | |
|---|---|---|
| WO | 98/26799 | 6/1998 |
| WO | 2005/042564 | 5/2005 |
| WO | 2007/053489 | 5/2007 |

OTHER PUBLICATIONS

Wang et al ; Infection and Immunity 2001, 69:4734-4741.*

Wang et al, Infection and Immunity 2001,69:4734-4741.*

Arya et al Vaccine. Dec. 1995;13(17):1727-8.*

Lohman, T.M., et al., *Escherichia coli* single-stranded DNA-binding protein: multiple DNA-binding modes and cooperativities. Annual Reviews in Biochemistry 63:527-70, 1994.

MacLennan, C.A. et al. The neglected role of antibody in protection against bacteremia caused by nontyphoidal strains of *Salmonella* in African children. J Clin. Invest. 118:1553-62, 2008.

Maurizi, M.R. and D. Xia, Protein Binding and Disruption by Clp/Hsp100 Chaperones. Structure (Camb). 12(2):175-83, 2004.

Miller et al. Nucleotide sequence of the partition locus of *Escherichia coli* plasmid pSC101, Gene 24:309-15, 1983.

Noriega FR, et al., Construction and characterization of attenuated ΔaroA ΔvirG *Shigella flexneri* 2a strain CVD 1203, a prototype live oral vaccine. Infect Immun 62:5168-5172, 1995.

Noriega FR, et al., Further characterization of ΔaroA, ΔvirG *Shigella flexneri* 2a strain CVD 1203 as a mucosal *Shigella* vaccine and as a live vector for delivering antigens of enterotoxigenic *Escherichia coli*. Infect Immun 64:23-27, 1996.

Noriega FR, et al., Engineered ΔguaBA ΔvirG *Shigella flexneri* 2a strain CVD 1205: construction, safety, immunogenicity, and potential efficacy as a mucosal vaccine. Infect Immun 64:3055-3061, 1996.

Ogushi, K. et al. *Salmonella enteritidis* FliC (flagella filament protein) induces human beta-defensin-2 mRNA production by Caco-2 cells. J. Biol. Chem. 276:30521-6, 2001.

Olanratmanee T, et al., Safety and immunogenicity of *Salmonella* Typhi Ty21a liquid formulation vaccine in 4- to 6- year-old Thai children. J Infect Dis 166:451-452, 1992.

Orr N, Galen JE, Levine MM. Expression and immunogenicity of a mutant diphtheria toxin molecule, CRM197, and its fragments in *Salmonella* Typhi vaccine strain CVD 908-htrA. Infect Immun 67:4290-4294, 1999.

Orr N, Galen JE, Levine MM. Novel use of anaerobically induced promoter, dmsA, for controlled expression of Fragment C of tetanus toxin in live attenuated *Salmonella enterica* serovar Typhi strain CVD 908-htrA. Vaccine 19:1694 1700, 2001.

Pasetti MF, et al., Attenuated ΔguaBA *Salmonella* Typhi vaccine strain CVD 915 as a live vector utilizing prokaryotic or eukaryotic expression systems to deliver foreign antigens and elicit immune responses. Clin Immun 92:76-89, 1999.

Pasetti MF, et al., Mechanisms and cellular events associated with the priming of mucosal and systemic immune responses to *Salmonella enterica* serovar Typhi live vector vaccines delivered intranasally in the murine model. Vaccine 18:3208-3213, 2000.

Pasetti, M, et al., Animal models paving the way for clinical trials of attenuated *Salmonella enterica* serovar Typhi live oral vaccines and live vectors. Vaccine. 21:401-18, 2003.

Pasetti MF, et al., Attenuated *Salmonella* enterica serovar Typhi and *Shigella flexneri* 2a strains mucosally deliver DNA vaccines encoding measles virus hemagglutinin, inducing specific immune responses and protection in cotton rats. J Virol 77:5209-5217, 2003.

Pickard D, et al., Characterization of defined ompR mutants of *Salmonella Typhi*: ompR is involved in the regulation of Vi polysaccharide expression. Infect Immun 62:3984-3993, 1994.

(Continued)

*Primary Examiner* — Padma V Baskar

(74) *Attorney, Agent, or Firm* — Roylance, Abrams, Berdo & Goodman, L.L.P.

(57) ABSTRACT

The present invention is drawn to a live, attenuated *S. Paratyphi* A strain, a live, attenuated *S. Paratyphi* A strain comprising a stabilized plasmid expression system, and methods of using these strains.

6 Claims, 8 Drawing Sheets

OTHER PUBLICATIONS

Pratt, L.A. et al., From acids to osmZ: multiple factors influence synthesis of the OmpF and OmpC porins in *Escherichia coli*. Molecular Microbiology 20:911-7, 1996.
Salerno-Goncalves R, et al., Concomitant Induction of CD4(+) and CD8(+) T Cell Responses in Volunteers Immunized with *Salmonella* enterica Serovar Typhi Strain CVD 908-htrA. J Immol. 170:2734-2741, 2003.
Servos S, et al., Molecular cloning and characterization of the aroD gene encoding 3-dehydroguinase from *Salmonella Typhi*. J Gen Micro 137:147-152, 1990.
Sztein MB, et al., Cytokine production patterns and lymphoproliferative responses in volunteers orally immunized with attenuated vaccine strains of *Salmonella Typhi*. J Infect Dis 170:1508-1517, 1994.
Sztein MB, et al., Cytotoxic T lymphocytes after oral immunization with attenuated strains of *Salmonella Typhi* in humans. J Immunol 155:3987-3993, 1995.
Tacket Co, et al., Lack of immune response to the Vi component of a Vi-positive variant of the *Salmonella Typhi* live oral vaccine strain Ty21a in volunteer studies. J Infect Dis 163:901-904, 1991.
Tacket Co, et al., Comparison of the safety and immunogenicity of ΔaroC ΔaroD and Δcya Δcrp *Salmonella typhi* strains in adult volunteers. Infect Immun 60:536-541, 1992.
Tacket Co, et al., Clinical acceptability and immunogenicity of CVD 908 *Salmonella Typhi* vaccine strain. Vaccine 10:443-446, 1992.
Tacket Co, et al., Safety of live oral *Salmonella typhi* vaccine strains with deletions in htrA and aroC aroD and immune response in humans. Infect Immun 65:452-456, 1997.
Tacket Co, et al., Safety and immunogenicity in humans of an attenuated *Salmonella* Typhivaccine vector strain expressing plasmid-encoded hepatitis B antigens stabilized by the Asd-balanced lethal system. Infect Immun 65:3381-3385, 1997.
Tacket Co, et al., Phase 2 clinical trial of attenuated *Salmonella enterica* serovar Typhi oral live vector vaccine CVD 908-htrA in U.S. volunteers. Infect Immun 68:1196-1201, 2000.
Tacket Co, et al., Safety and immune responses to attenuated *Salmonella enterica* serovar Typhi oral live vector vaccines expressing tetanus toxin fragment C. Clin Immunol 97:146-153, 2000.
Tacket Co, et al., Immune responses to an oral Typhoid vaccine strain modified to constitutively express Vi capsular polysaccharide. J Infect Dis, 190:565-570, 2004.
Van de Verg L, et al., Specific IgA secreting cells in peripheral blood following oral immunization with bivalent *Salmonella* Typhi/ *Shigella sonnei* vaccine or infection with pathogenic *S. sonnei* in humans. Infect Immun 58:2002-2004, 1990.
Vindurampulle CJ, et al., Recombinant *Salmonella enterica* serovar Typhi in a prime-boost strategy. Vaccine 22 (27-28):3744-3750, 2004.
Wang JY, et al., Constitutive expression of the Vi polysaccharide capsular antigen in attenuated *Salmonella enterica* serovar Typhi oral vaccine strain CVD 909. Infect Immun 68:4647-4652, 2000.
Wang JY, et al., Construction, genotypic and phenotypic characterization, and immunogenicity of attenuated ΔguaBA *Salmonella enterica* serovar Typhi strain CVD 915. Infect Immun 69:4734-4741, 2001.
Wu S, et al., Construction and immunogenicity in mice of attenuated *Salmonella* Typhi expressing *Plasmodium falciparum* merozoite surface protein (MSP-1) fused to tetanus toxin fragment C. J Biotechnol. 83:125 135, 2000.
Yamamoto, T. et al., Disruption of the Genes for CIpXP Protease in *Salmonella enterica* Serovar Typhimurium Results in Persistent Infection in Mice, and Development of Persistence Requires Endogenous Gamma Interferon and Tumor Necrosis Factor Alpha. Infect Immun. 69(5):3164-74, 2001.
Yoon, S.S. et al. Decreased potency of the Vibrio cholerae sheathed flagellum to trigger host innate immunity. Infect. Immun. 76:1282-8, 2008.
Komoriya, K. et al., Flagellar proteins and type III-export virulence factors. Molecular Microbiology 34:767-779, 1999.
Brett, P.J., et al., Structural and immunological characterization of *Burkholderia pseudomallei* O-polysaccharideFlagellin protein conjugates. Infect. Immun. 64:2824-2828, 1996.
Thomsen, *Salmonella* genes required for virulence and stress response. Characterization of CIpP and RfbM [online] Ph.D. Thesis, Dept. Vet. Micro. The Royal Vet. Agric. Univ. Denmark, Jan. 2002, pp. 1-148. Available online at: http://curis.ku.dk/portal-life/files/13549041/Line$_{Elnif}$_Thomsen.pdf.
International Search Report for PCT/US06/042148, dated Feb. 24, 2011.
Altboum Z, et al., Attenuated *Shigella flexneri* 2a ΔguaBA strain CVD 1204 expressing ETEC CS2 and CS3 fimbriae as a live mucosal vaccine against Shigella and enterotoxigenic *Escherichia coli* infection. Infect Immun 69:3150 8, 2001.
Anderson RJ, et al., ΔguaBA attenuated *Shigella flexneri* 2a strain CVD 1204 as a *Shigella* vaccine and as a live mucosal delivery system for fragment C of tetanus toxin. Vaccine 18:2193-2202, 2000.
Barry EM, et al., Expression and immunogenicity of pertussis toxin S1 subunit tetanus toxin fragment C fusions in *Salmonella* Typhi vaccine strain CVD 908. Infect Immun 64:4172-4181, 1996.
Bhan, M.K. et al. Typhoid and paratyphoid fever. Lancet 366:749-762, 2005.
Black RE, et al., Efficacy of one or two doses of Ty21a *Salmonella Salmonella* Typhi vaccine in enteric-coated capsules in a controlled field trial. Vaccine 8:81-84, 1990.
Capozzo AV, et al., Mucosally delivered *Salmonella* live vector vaccines elicit potent immune responses against a foreign antigen in neonatal mice born to naive and immune mothers. Infect Immun 72:4637-4646, 2004.
Carlini, L.E., et al., Viability and preliminary in vivo characterization of site-directed mutants of *Escherichia coli* singlestranded DNA-binding protein. Mol. Microbiol. 10:1067-1075, 1993.
Chase et al., Single-stranded DNA binding proteins required for DNA replication. Annual Reviews in Biochemistry 55:103-36, 1986.
Chatfield SN, et al., Construction of a genetically defined *Salmonella Typhi* Ty2 aroA, aroC mutant for the engineering of a candidate live oral typhoid-tetanus vaccine. Vaccine 10:8-11, 1992.
Conner, A.C. et al., Typhoid and paratyphoid fever in travelers. Lancet Infect Dis. 5(10):623-628, 2005.
Cryz SJ, et al., Randomized double-blind placebo-controlled trial to evaluate the safety and immunogenicity of the live oral cholera vaccine strain CVD 103-HgR in adult Swiss. Vaccine 8:577-580, 1990.
Cryz SJ Jr, et al., Safety and immunogenicity of *Salmonella Typhi* Ty21a vaccine in young children. Infect Immun 61:1149-115, 1993.
Cryz SJ Jr, et al., Safety and immunogenicity of a live oral bivalent typhoid fever (*Salmonella* Typhi-Ty21a) cholera (Vibrio cholerae CVD 103-HgR) vaccine in healthy adults. Infect Immun 63:1336-1339, 1995.
Datsenko and Wanner, One-step inactivation of chromosomal genes in *Escherichia coli* K-12 using PCR products. PNAS USA 97:6640-6645, 2000.
Egger, L.A. et al., Signal transduction via the histidyl-aspartyl phosphorelay. Genes to Cells 2:167-84, 1997.
Ellis, R.W. et al., Combination vaccines. Advances in Pharm. 39:393-423, 1997.
Feuillet, V. et al. Involvement of Toll-like receptor 5 in the recognition of flagellated bacteria. PNAS 103:12487-92, 2006.
Ferreccio C, et al., Comparative efficacy of two, three, or four doses of Ty21A live oral typhoid vaccine in enteric coated capsules: a field trial in an endemic area. J Infect Dis 159:766 769, 1989.
Funnell, B.E. and R.A. Slavcev. Table 1 of Chapter 5, Partition Systems of Bacterial Plasmids. In Plasmid Biology. 2004. Be Funnell and GJ Phillips, eds. ASM Press, Washington, DC.
Galen JE, et al., Optimization of plasmid maintenance in the attenuated live vector vaccine *Salmonella* Typhi strain CVD 908-htrA. Infect Immun 67:6424-6433, 1999.
Galen JE, Levine MM. Can a "flawless" live vector vaccine strain be engineered? Trends Microbiol 9:372-376, 2001.
Galen JE, et al., Adaptation of the endogenous *Salmonella enterica* serovar Typhi clyA-encoded hemolysin for antigen export enhances the immunogenicity of anthrax protective antigen domain 4 expressed by the attenuated live vector vaccine strain CVD 908-htrA. Infect Immun 72:7096-7106, 2004.
Gewirtz, A.T. et al. Cutting edge: bacterial flagellin activates basolaterally expressed TLR5 to induce epithelial proinflammatory gene expression. J. Immunol. 167:1882-5, 2001.

Gómez-Duarte, OG, et al., Expression of fragment C of tetanus toxin fused to a carboxyl-terminal fragment of diphtheria toxin in *Salmonella Typhi* CVD 908 vaccine strain. Vaccine 13:1596-1602, 1995.
Gómez-Duarte O, et al., Expression, secretion and immunogenicity of the *Plasmodium falciparum* SSP-2 protein in *Salmonella* vaccine strains by a type I secretion system. Infect Immun 69:1192-1198, 2001.
Gonzalez C, et al., *Salmonella* Typhi strain CCD 908 expressing the circumsporozoite protein of *Plasmodium falciparum*: strain construction, safety and immunogenicity. J Infect Dis 169:927-931, 1994.
González CR, et al., Immunogenicity of a *Salmonella* Typhi CVD 908 candidate vaccine strain expressing the major surface protein gp63 of *Leishmania mexicana* mexicana. Vaccine 16:9/10 1043-1052, 1998.
Herrington DA, et al., Studies in volunteers to evaluate candidate *Shigella* vaccines: further experience with a bivalent *Salmonella* Typhi-*Shigella sonnei* vaccine and protection conferred by previous *Shigella sonnei* disease. Vaccine 8:353-357, 1990.
Hone DM, et al., Construction of genetically-defined double aro mutants of *Salmonella* Typhi. Vaccine 9:810-816, 1991.
Hone DM, et al., Evaluation in volunteers of a candidate live oral attenuated *Salmonella* Typhi vaccine. J Clin Invest 90:412-420, 1992.
Hone DM, et al., Construction and characterization of isogenic O-antigen variants of *Salmonella* Typhi. Molec Microbiol 13:525-530, 1994.
Huleatt, J.W. et al. Vaccination with recombinant fusion proteins incorporating Toll-like receptor ligands induces rapid cellular and humoral immunity. Vaccine. 25:763-75, 2007.
Ibrahim, G.F. et al. Method for the isolation of highly purified *Salmonella flagellins*. J. Clin. Microbiol. 22:1040-4, 1985.
Konadu E et al. Synthesis, characterization, and immunological properties in mice of conjugates composed of detoxified lipopolysaccharide of *Salmonella paratyphi* a bound to tetanus toxoid with emphasis on the role of O acetyls. Infect Immun 64(7):2709-15, 1996.
Koprowski H, et al., Attenuated *Shigella flexneri* 2a vaccine strain CVD 1204 expressing colonization factor antigen I and mutant heat labile enterotoxin of enterotoxigenic *Escherichia coli*. Infect Immun 68:4884 92, 2000.
Kotloff K, et al., Safety, immunogenicity and transmissibility in humans of CVD 1203, a live oral Shigella flexneri 2a vaccine candidate attenuated by deletions in aroA and virG. Infect Immun 64:4542-4548, 1996.
Kotloff KL, et al., *Shigella flexneri* 2a strain CVD 1207 with specific deletions in virG, sen, set and guaBA is highly attenuated in humans. Infect Immun 68:1034-39, 2000.
Kotloff KL, et al., Phase I evaluation of ΔvirG *Shigella sonnei* live, attenuated, oral vaccine strain WRSS1 in healthy adults. Infect Immun 70:2016-21, 2002.
Kotloff KL, et al., Deletion in the *Shigella* enterotoxin genes further attenuates *Shigella flexneri* 2a bearing guanine auxotrophy in a Phase 1 trial of CVD 1204 and CVD 1208. J Infect Dis 190:1745-1754, 2004.
Levine MM, et al., Safety, infectivity, immunogenicity and in vivo stability of two attenuated auxotrophic mutant strains of *Salmonella* Typhi, 541Ty and 543Ty, as live oral vaccines in man. J Clin Invest 79:888 902, 1987.
Levine MM, et al., Large scale field trial of Ty21a live oral typhoid vaccine in enteric coated capsule formulation. Lancet 1:1049 1052, 1987.
Levine M.M., et al., Safety, Immunogenicity, and Efficacy of Recombinant Live Oral Cholera Vaccines, CVD 103 and CVD 103-hgr. Lancet 332: 467-470, 1988.
Levine MM, et al., Progress in vaccines against typhoid fever. Rev Infect Dis 2 (supplement 3):S552 S567, 1989.
Levine MM, et al., Attenuated *Salmonella* as carriers for the expression of foreign antigens. Microecology and Therapy 19:23-32, 1989.
Levine MM, et al., Comparison of enteric-coated capsules and liquid formulation of Ty21a typhoid vaccine in a randomized controlled field trial. Lancet 336:891-894, 1990.
Levine MM, et al., Clinical and field trials with attenuated *Salmonella* Typhi as live oral vaccines and as "carrier vaccines". Res Microbiol 141:807-816, 1990.
Levine MM, et al., Attenuated *Salmonella* as live oral vaccines against typhoid fever and as live vectors. J Biotechnology 44:193-196, 1996.
Levine MM, et al., Attenuated *Salmonella* Typhi and *Shigella* as live oral vaccines and as live vectors. Behring Inst Mitt 98:120-123, 1997.
Levine MM, et al., Duration of efficacy of Ty21a, attenuated *Salmonella* Typhi live oral vaccine. Vaccine 17:2 Supplement S22-S27, 1999.
Liu S-L, et al., The chromosome of *Salmonella* paratyphiA is inverted by recombination between rrnH and rrnG. J. Bacteriol. 177(22):6585-6592, 1995.

* cited by examiner

SEQUENCE LISTING

```
<160> NUMBER OF SEQ ID NOS: 40

<210> SEQ ID NO 1
<211> LENGTH: 489
<212> TYPE: DNA
<213> ORGANISM: Artificial Sequence
<220> FEATURE:
<223> OTHER INFORMATION: Chemically-synthesized mutated guaBA region

<400> SEQUENCE: 1

ggaacatcgc acagcgcacc tgagcggtat cgtctttgag cgtaaagtac cagtggcccg     60

acgcaggctg cgtgaaatta gaaatctcgc cgctgatcca tacctgtccc atctcctgtt    120

ctaacagcag acgaaccgtc tggttaaggc ggcttacggt aaaaattgag gaagtttgag    180

aggataacat gtgagcggga tcaaattcta aatcagcagg ttattcaatc ggtgtaggct    240

ggagcctgct tcgaagttcc tatactttct agagaatagg aacttcggaa taggaactaa    300

ggaggatatt catatgctct ctctctgcgt gctgtcgaaa ccatcgactt tatgaccgcg    360

cactgggcgc acctgccgta tgacttcctg ggtcgtgttt ccaaccgcat catcaatgaa    420

gtcaacggga tttcccgtgt ggtgtatgac atcagcggta aaccaccggc taccattgag    480

tgggaatga                                                            489


<210> SEQ ID NO 2
<211> LENGTH: 634
<212> TYPE: DNA
<213> ORGANISM: Artificial Sequence
<220> FEATURE:
<223> OTHER INFORMATION: Chemically-synthesized mutated clpX region

<400> SEQUENCE: 2

cctgagaatg gcatttgcgt cgtcgtgtgc ggcacaaaga acaaagaaga ggttttgact     60

catgacagat aaacgcaaag atggctcggg caaattgttg tactgctctt tttgcggcaa    120

aagccagcat gaagtgcgca agctgattgc cggtccatcc gtgtatatct gcgacgaatg    180

cgtcgattta tgtaacgaca ttattcgcgc ccttatatat atgcggccgc tgtaggctgg    240
```

-continued

```
agctgcttcg aagttcctat actttctaga gaataggaac ttcggaatag gaactaagga    300

ggatattcat atggcgcgcc tataagggcg aattccgtga cgaagcgctg aacgctatcg    360

ccaggaaagc aatggcgcgt aaaaccggtg cccgtggtct gcgttctatc gtcgaagcgg    420

cgctgctgga taccatgtac gatttgccat ctatggaaga cgtcgaaaaa gtggtgatcg    480

acgagtccgt tattgccggt cagagtaagc cgttgctgat ttacggcaaa ccggaagcgc    540

aggcttctgg cgaataatta aacattcata caatcagtta gccaaaaaag gggggatttt    600

atctcccctt tcgtttttcc tgtaaacacg ccgt                                634
```

<210> SEQ ID NO 3
<211> LENGTH: 370
<212> TYPE: DNA
<213> ORGANISM: Artificial Sequence
<220> FEATURE:
<223> OTHER INFORMATION: Chemically-synthesized mutated clpP region

<400> SEQUENCE: 3

```
tccatcaggt tacaatcagt acagcaggtt ttttcaattt ttatccagga gacggaaatg     60

tcatacagcg gagaacgaga taatttggcc cctcatatat gaatatcctc cttagttcct    120

attccgaagt tcctattctc tagaaagtat aggaacttcg aagcagctcc agcctacacg    180

ctaggactca attttgaccc atcgtaattg atgccctgga cgcaagtgtg ccgctataca    240

cttcatcctt cacgctacct cggtgttggt tgccagcgcg cctcccggtg acttacttat    300

gtaagcgcct gcggagtcgc cgagttgccg ccttgatgta gctcgaatga ttttgtgtat    360

atactaatga                                                           370
```

<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4

```
ctgcagtcat tcccactcaa tggtagc                                         27
```

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5

```
ggaacatcgc acagcgca                                                   18
```

<210> SEQ ID NO 6
<211> LENGTH: 17
<212> TYPE: DNA
<213> ORGANISM: Artificial Sequence
<220> FEATURE:
<223> OTHER INFORMATION: Synthetic primer

<400> SEQUENCE: 6

```
gtgtaggagc tgcttcg                                                    17
```

<210> SEQ ID NO 7
<211> LENGTH: 20
<212> TYPE: DNA
<213> ORGANISM: Artificial Sequence -continued
<220> FEATURE:
<223> OTHER INFORMATION: Synthetic primer

<400> SEQUENCE: 7
catatgaata tcctccttag 20

<210> SEQ ID NO 8
<211> LENGTH: 119
<212> TYPE: DNA
<213> ORGANISM: Artificial Sequence
<220> FEATURE:
<223> OTHER INFORMATION: Synthetic primer

<400> SEQUENCE: 8
cgaaccgtct ggttaaggcg gcttacggta aaaattgagg aagtttgaga ggataacatg 60
tgagcgggat caaattctaa atcagcaggt tattcaatcg tgtaggctgg agctgcttc 119

<210> SEQ ID NO 9
<211> LENGTH: 120
<212> TYPE: DNA
<213> ORGANISM: Artificial Sequence
<220> FEATURE:
<223> OTHER INFORMATION: Synthetic primer

<400> SEQUENCE: 9
ttcattgatg atgcggttgg aaacacgacc caggaagtca tacggcaggt gcgcccagtg 60
cgcggtcata aagtcgatgg tttcgacagc acgcagagag catatgaata tcctccttag 120

<210> SEQ ID NO 10
<211> LENGTH: 28
<212> TYPE: DNA
<213> ORGANISM: Artificial Sequence
<220> FEATURE:
<223> OTHER INFORMATION: Synthetic primer

<400> SEQUENCE: 10
gaaggagtat tgcccatgct acgtatcg 28

<210> SEQ ID NO 11
<211> LENGTH: 42
<212> TYPE: DNA
<213> ORGANISM: Artificial Sequence
<220> FEATURE:
<223> OTHER INFORMATION: Synthetic primer

<400> SEQUENCE: 11
catatgaagg agtattgccc atgctacgta tcgctaaaga ag 42

<210> SEQ ID NO 12
<211> LENGTH: 36
<212> TYPE: DNA
<213> ORGANISM: Artificial Sequence
<220> FEATURE:
<223> OTHER INFORMATION: Synthetic primer

<400> SEQUENCE: 12
atgcatctgc agtcattccc actcaatggt agccgg 36

<210> SEQ ID NO 13
<211> LENGTH: 30
<212> TYPE: DNA
<213> ORGANISM: Artificial Sequence
<220> FEATURE:
<223> OTHER INFORMATION: Synthetic primer

<400> SEQUENCE: 13
acagataaac gcaaagatgg ctcgggcaaa 30

<210> SEQ ID NO 14
<211> LENGTH: 30
<212> TYPE: DNA
<213> ORGANISM: Artificial Sequence
<220> FEATURE:
<223> OTHER INFORMATION: Synthetic primer

<400> SEQUENCE: 14
ttattcgcca gaagcctgcg cttccggttt 30

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
cctgagaatg gcatttgcgt cgtcgtgtgc 30

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
acggcgtgtt tacaggaaaa acgaaagggg 30

<210> SEQ ID NO 17
<211> LENGTH: 30
<212> TYPE: DNA
<213> ORGANISM: Artificial Sequence
<220> FEATURE:
<223> OTHER INFORMATION: Synthetic primer

<400> SEQUENCE: 17
tcatacagcg gagaacgaga taatttggcc 30

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
ttacataagt aagtcactgg gaggcgcgct 30

<210> SEQ ID NO 19
<211> LENGTH: 30
<212> TYPE: DNA
<213> ORGANISM: Artificial Sequence
<220> FEATURE:
<223> OTHER INFORMATION: Synthetic primer

<400> SEQUENCE: 19
tccatcaggt tacaatcagt acagcagatt 30

<210> SEQ ID NO 20
<211> LENGTH: 30
<212> TYPE: DNA
<213> ORGANISM: Artificial Sequence
<220> FEATURE:
<223> OTHER INFORMATION: Synthetic primer

<400> SEQUENCE: 20
tcattagtat atacacaaaa tcattcgagc 30

<210> SEQ ID NO 21
<211> LENGTH: 45
<212> TYPE: DNA
<213> ORGANISM: Artificial Sequence
<220> FEATURE:
<223> OTHER INFORMATION: Synthetic primer

<400> SEQUENCE: 21
gcggccgcga aggagagacg gaaatgtcat acagcggaga acgag 45

<210> SEQ ID NO 22
<211> LENGTH: 42
<212> TYPE: DNA
<213> ORGANISM: Artificial Sequence
<220> FEATURE:
<223> OTHER INFORMATION: Synthetic primer

<400> SEQUENCE: 22
tcgcgagaat tcttacataa gtaagtcact gggaggcgcg ct 42

<210> SEQ ID NO 23
<211> LENGTH: 45
<212> TYPE: DNA
<213> ORGANISM: Artificial Sequence
<220> FEATURE:
<223> OTHER INFORMATION: Synthetic primer

<400> SEQUENCE: 23
gcggccgcga aggagtttga ctcatgacag ataaacgcaa agatg 45

<210> SEQ ID NO 24
<211> LENGTH: 36
<212> TYPE: DNA
<213> ORGANISM: Artificial Sequence
<220> FEATURE:
<223> OTHER INFORMATION: Synthetic primer

<400> SEQUENCE: 24
catatgttat tcgccagaag cctgcgcttc cggttt 36

<210> SEQ ID NO 25
<211> LENGTH: 38
<212> TYPE: DNA
<213> ORGANISM: Artificial Sequence
<220> FEATURE:
<223> OTHER INFORMATION: Synthetic primer

<400> SEQUENCE: 25
gcggccgctt acataagtaa gtcactggga ggcgcgct 38

<210> SEQ ID NO 26
<211> LENGTH: 3120
<212> TYPE: DNA
<213> ORGANISM: Salmonella typhi

<400> SEQUENCE: 26
ttgcccatgc tacgtatcgc taaagaagcc ctgacgtttg acgacgtcct ccttgttccc 60
gctcactcca ccgttttgcc gaatactgct gatctcagca cgcagttgac gaaaactatt 120
cgtctgaata ttcctatgct ttctgcggcg atggacaccg tgacggaagc gcgcctggca 180

-continued

```
attgccctgg cccaggaagg cggcatcggt tttatccaca aaaacatgtc tattgagcgc     240
caggcggaag aagttcgccg cgtgaagaaa cacgagtccg gcgtagtgac cgacccgcag     300
accgtcctgc caaccaccac gttgcatgaa gtgaaagccc tgaccgagcg taacggtttt     360
gcgggctatc cggtggtgac tgaagataac gagctggtgg gtatcatcac cggtcgtgac     420
gtgcgttttg tgactgacct gaaccagccg gtgagtgttt acatgacgcc gaaagagcgt     480
ctggtgaccg ttcgtgaagg cgaagcccgt gaagtcgtgc tggcaaaaat gcacgaaaaa     540
cgcgtagaaa aagcgctggt cgttgatgat aacttccatc tgcttggcat gattaccgta     600
aaagatttcc agaaagcgga acgtaaacca aactcctgta aagatgagca gggccgttta     660
cgtgtcggcg cggcggtcgg cgcaggcgcg ggcaacgaag agcgcgttga cgcgctggtg     720
gcggcaggcg ttgacgtcct gctgatcgac tcttctcacg gtcactctga aggcgtgttg     780
caacgtatcc gtgaaacccg tgctaaatat cctgacctgc aaatcatcgg cggcaacgtc     840
gcgacgggcg caggcgctcg cgcactggcg gaagccggtt gcagcgcggt gaaagtcggt     900
atcggcccgg gttccatctg taccactcgt atcgtgactg gcgtgggcgt tccgcagatt     960
accgctgttt ctgacgcagt tgaagcgctg gaaggcaccg ggattccggt tatcgctgac    1020
ggcggtatcc gtttctccgg cgacatcgcc aaagccatcg ccgcaggcgc gagcgctgtc    1080
atggtcggtt ctatgctggc gggtaccgaa gaatccccgg gcgaaatcga actctaccag    1140
ggccgttctt acaaatctta ccgcggcatg ggctcgctgg gcgcgatgtc caaaggttcc    1200
tctgaccgtt acttccagag cgacaacgcc gccgacaaac tggtgccgga aggtatcgaa    1260
ggccgcgtag cctataaagg tcgcctgaaa gagatcattc accagcagat gggcggcctg    1320
cgctcctgta tggggctgac cggttgtgct accatcgacg aactgcgtac taaagcggag    1380
tttgtgcgta tcagcggtgc gggtatccag gaaagccacg ttcacgacgt gaccatcacc    1440
aaagagtccc cgaactaccg tctgggctcc tgattttctt cgcccgacct tcgcgtcggg    1500
cgatttattt aatctgtttc acttgcctcg gaataagcgt caatgacgga aaacattcat    1560
aagcatcgca tcctcattct ggacttcggt tctcagtaca ctcaactggt tgcgcgccgc    1620
gtgcgtgagc tgggtgttta ctgcgaactg tgggcgtggg atgtgacaga agcacaaatt    1680
cgtgacttca acccaagcgg cattattctt tccggcggcc cggaaagcac caccgaagaa    1740
aacagcccgc gcgcgccgca gtatgtcttt gaagcaggcg tgccggtatt tggcgtctgc    1800
tacgggatgc agaccatggc gatgcagctt ggcggtcatg tagaaggttc taatgagcgt    1860
gaatttggtt acgcgcaggt cgaagtgctg accgacagcg cgctggttcg cggtattgaa    1920
gattccctga ccgccgacgg caaaccgctg ctggacgtgt ggatgagcca cggcgataaa    1980
gtgacggcga ttccgtccga cttcgtgacc gtagccagca ccgaaagctg cccgttcgcc    2040
atcatggcta acgaagaaaa acgcttctac ggcgtacagt tccacccgga agtgactcac    2100
acccgccagg gtatgcgcat gctggagcgt tttgtgcgtg atatctgcca gtgtgaagcc    2160
ctgtggacgc cggcgaagat catcgacgac gccgtggcgc gcattcgcga gcaggtaggc    2220
gacgataaag tgatcctcgg tctctccggc ggcgtggatt cttccgtaac cgcaatgctg    2280
ctgcaccgcg cgatcggtaa aaatctgacc tgtgtattcg tcgacaacgg cctgctgcgt    2340
ctcaacgaag ccgagcaggt gatggacatg tttggcgacc attttggtct gaacatcgtt    2400
cacgtaccgg cagaagatcg cttcctgtcc gcgttggctg gcgaaaacga tccggaagcg    2460
aagcgtaaga tcattggccg tgtttttgtg gaagtgttcg acgaagaagc gttgaaactg    2520
gaagacgtga aatggctggc gcagggcacc atctaccctg acgtcatcga atctgcggcg    2580
```

-continued tctgcaaccg gtaaagcgca cgtcatcaaa tctcaccaca atgttggcgg cctgccgaaa 2640
gagatgaaga tggggctggt tgaaccgctg aaagagctgt tcaaagacga agtgcgtaag 2700
attggtctgg agctgggcct gccgtacgac atgctgtacc gtcatccgtt cccggggccg 2760
ggcctcggcg tacgtgtact gggtgaagtg aagaaagagt actgcgacct gctgcgccgt 2820
gctgatgcca tcttcattga agagctgcgt aaggcggatc tgtacgacaa agtcagccag 2880
gcgttcaccg tcttcctgcc agtacgctcc gttggcgtaa tgggcgatgg tcgtaagtac 2940
gattgggtgg tctctctgcg tgctgtcgaa accatcgact ttatgaccgc gcactgggcg 3000
cacctgccgt atgacttcct gggtcgtgtt tccaaccgca tcatcaatga agtcaacggg 3060
atttcccgtg tggtgtatga catcagcggt aaaccaccgg ctaccattga gtgggaataa 3120

<210> SEQ ID NO 27
<211> LENGTH: 2147
<212> TYPE: DNA
<213> ORGANISM: Salmonella typhi

<400> SEQUENCE: 27
ttattcgcca gaagcctgcg cttccggttt gccgtaaatc agcaacggct tactctgacc 60
ggcaataacg gactcgtcaa tcaccacttt ttcgacgtct tccatagatg gcaaatcgta 120
catggtatcc agcagcgccg cttcgacgat agaacgcagg ccacgggcac cagttttacg 180
cgccatcgct ttcctggcga tagcgttcag cgcttcgtca cggaattcca gatcgacgcc 240
ttccaggtta aacagcgcct gatactgctt ggtcagcgca tttttcggct ctttcaggat 300
ttgaaccagc gcttcttcgc tgagttcgtt cagcgtcgcc accactggca gacgaccgat 360
aaactcagga atcagaccaa atttgatcaa atcttccggt tcaacctgcg acaacagctc 420
gccttcactg gctttgtcgg acttcgcttt caccgtcgcg ccaaaaccaa tgccggagcc 480
ggtttcaaca cggttagcga tcactttatc cagaccggca aacgcgccgc cgcagataaa 540
cagaatctta gaggtatcta cctgtaagaa ctcctgctgc ggatgtttgc gaccgccctg 600
cggtggaacc gcggcgacgg tgccttcgat cagtttcagc aacgcctgct gtacgccttc 660
gccggaaaca tcgcgggtaa tggacggatt gtctgattta cgcgaaatct tatcgatttc 720
atcaatgtag acaatcccac gctgcgcttt ttgcacgtcg tagtcgcatt tctgcaacag 780
tttctgaatg atattctcga cgtcttcccc cacgtaaccc gcttcggtca gcgtggtcgc 840
atccgccata gtgaacggca catccagcaa gcgcgccagc gtttccgcca gcagcgtttt 900
accggaaccg gtcggtccag tcagcagaat gttgcttttg cctaactcga cgccattgct 960
ggtatcgccg ttacgcagac gcttgtagtg gttatagacc gccaccgcca gcactttttt 1020
cgcctgctcc tggccgataa cgtaatcgtc caggtgagta cgaatttcat gcggcgtcgg 1080
cagcgcacta cgttcacggt gcggagcaac ttctttaatt tcttcgcgaa taatgtcgtt 1140
acataaatcg acgcattcgt cgcagatata cacggatgga ccggcaatca gcttgcgcac 1200
ttcatgctgg cttttgccgc aaaaagagca gtacaacaat ttgcccgagc catctttgcg 1260
tttatctgtc atgagtcaaa acctcttctt tgttctttgt gccgcacacg acgacgcaaa 1320
tgccattctc aggcgcaagc cgctaatcag cgttgtgccg cccttcatta gtatatacac 1380
aaaatcattc gagctacatc aaggcggcaa ctcagcgact ccgcaggcgc ttacataagt 1440
aagtcactgg gaggcgcgct ggcaaccaac accgaggtag cgtgaaggat gaagtgtata 1500
gcggcacact tgcgtccagg gcatcaatta cgatgggtca aaattgagtc aaccaaaccg 1560
tactctaccg cttcaggcgc ggagaggaag cgatcgcgct cagtatcacg ttcaatctgc 1620

-continued

```
tcaagagatt gacccgtatg atgcgccata agttcattca tgcgcccttt tactttcaaa   1680

atttcgcggg cgtgaatttc aatatccgtc gcctggccct gatagccgcc cagcggctgg   1740

tggatcatga cgcgagagtt cggcaagcag aaacgtttgc ctttcgcccc ggcagtcagc   1800

agaaacgccc ccatagaggc cgcctgtccc atacaaatgg tgctgacgtc tggcttaata   1860

aactgcatgg tgtcatagat ggacatcccc gcagtaatta cgccgccagg agaattaatg   1920

tacagataga tatctttttc cgggttttcc gcttccagga acagcatctg cgccacgatc   1980

aggttagcca tatggtcttc gacctggccg gtcagaaata tgacgcgttc cttaagtaga   2040

cgagaataga tatcaaaaga gcgctcaccg cgtgaggtct gttcaatgac catcggcacc   2100

agcgccatat gaggggccaa attatctcgt tctccgctgt atgacat                2147
```

```
<210> SEQ ID NO 28
<211> LENGTH: 687
<212> TYPE: DNA
<213> ORGANISM: Escherichia coli

<400> SEQUENCE: 28

cctagggcca gcaaaaggcc aggaaccgta aaaaggccgc gttgctggcg tttttccata     60

ggctccgccc ccctgacgag catcacaaaa atcgacgctc aagtcagagg tggcgaaacc    120

cgacaggact ataaagatac caggcgtttc cccctggaag ctccctcgtg cgctctcctg    180

ttccgaccct gccgcttacc ggatacctgt ccgcctttct cccttcggga agcgtggcgc    240

tttctcatag ctcacgctgt aggtatctca gttcggtgta ggtcgttcgc tccaagctgg    300

gctgtgtgca cgaacccccc gttcagcccg accgctgcgc cttatccggt aactatcgtc    360

ttgagtccaa cccggtaaga cacgacttat cgccactggc agcagccact ggtaacagga    420

ttagcagagc gaggtatgta ggcggtgcta cagagttctt gaagtggtgg cctaactacg    480

gctacactag aaggacagta tttggtatct gcgctctgct gaagccagtt accttcggaa    540

aaagagttgg tagctcttga tccggcaaac aaaccaccgc tggtagcggt ggtttttttg    600

tttgcaagca gcagattacg cgcagaaaaa aaggatctca agaagatcct ttgatctttt    660

ctacggggtc tgacgctcag tagatct                                        687
```

```
<210> SEQ ID NO 29
<211> LENGTH: 635
<212> TYPE: DNA
<213> ORGANISM: Salmonella typhimurium

<400> SEQUENCE: 29

cctaggagat acttaacagg gaagtgagag ggccgcggca aagccgtttt tccataggct     60

ccgcccccct gacaagcatc acgaaatctg acgctcaaat cagtggtggc gaaacccgac    120

aggactataa agataccagg cgtttccccc tggcggctcc ctcgtgcgct ctcctgttcc    180

tgcctttcgg tttaccggtg tcattccgct gttatggccg cgtttgtctc attccacgcc    240

tgacactcag ttccgggtag gcagttcgct ccaagctgga ctgtatgcac gaaccccccg    300

ttcagtccga ccgctgcgcc ttatccggta actatcgtct tgagtccaac ccggaaagac    360

atgcaaaagc accactggca gcagccactg gtaattgatt tagaggagtt agtcttgaag    420

tcatgcgccg gttaaggcta aactgaaagg acaagttttg gtgactgcgc tcctccaagc    480

cagttacctc ggttcaaaga gttggtagct cagagaacct tcgaaaaacc gccctgcaag    540

gcggtttttt cgttttcaga gcaagagatt acgcgcagac caaaacgatc tcaagaagat    600

catcttatta atcagataaa atatttctag gatct                               635
```

<210> SEQ ID NO 30
<211> LENGTH: 1955
<212> TYPE: DNA
<213> ORGANISM: Escherichia coli

<400> SEQUENCE: 30
cctaggtttc acctgttcta ttaggtgtta catgctgttc atctgttaca ttgtcgatct 60
gttcatggtg aacagcttta aatgcaccaa aaactcgtaa aagctctgat gtatctatct 120
tttttacacc gttttcatct gtgcatatgg acagttttcc ctttgatatc taacggtgaa 180
cagttgttct acttttgttt gttagtcttg atgcttcact gatagataca agagccataa 240
gaacctcaga tccttccgta tttagccagt atgttctcta gtgtggttcg ttgtttttgc 300
gtgagccatg agaacgaacc attgagatca tgcttacttt gcatgtcact caaaaatttt 360
gcctcaaaac tggtgagctg aatttttgca gttaaagcat cgtgtagtgt ttttcttagt 420
ccgttacgta ggtaggaatc tgatgtaatg gttgttggta ttttgtcacc attcattttt 480
atctggttgt tctcaagttc ggttacgaga tccatttgtc tatctagttc aacttggaaa 540
atcaacgtat cagtcgggcg gcctcgctta tcaaccacca atttcatatt gctgtaagtg 600
tttaaatctt tacttattgg tttcaaaacc cattggttaa gccttttaaa ctcatggtag 660
ttattttcaa gcattaacat gaacttaaat tcatcaaggc taatctctat atttgccttg 720
tgagttttct tttgtgttag ttcttttaat aaccactcat aaatcctcat agagtatttg 780
ttttcaaaag acttaacatg ttccagatta tattttatga atttttttaa ctggaaaaga 840
taaggcaata tctcttcact aaaaactaat tctaattttt cgcttgagaa cttggcatag 900
tttgtccact ggaaaatctc aaagccttta accaaaggat tcctgatttc cacagttctc 960
gtcatcagct ctctggttgc tttagctaat acaccataag cattttccct actgatgttc 1020
atcatctgag cgtattggtt ataagtgaac gataccgtcc gttctttcct tgtagggttt 1080
tcaatcgtgg ggttgagtag tgccacacag cataaaatta gcttggtttc atgctccgtt 1140
aagtcatagc gactaatcgc tagttcattt gctttgaaaa caactaattc agacatacat 1200
ctcaattggt ctaggtgatt ttaatcacta taccaattga gatgggctag tcaatgataa 1260
ttactagtcc ttttcctttg agttgtgggt atctgtaaat tctgctagac ctttgctgga 1320
aaacttgtaa attctgctag accctctgta aattccgcta gacctttgtg tgtttttttt 1380
gtttatattc aagtggttat aatttataga ataaagaaag aataaaaaaa gataaaaaga 1440
atagatccca gccctgtgta taactcacta ctttagtcag ttccgcagta ttacaaaagg 1500
atgtcgcaaa cgctgtttgc tcctctacaa aacagacctt aaaaccctaa aggcttaagt 1560
agcaccctcg caagctcggg caaatcgctg aatattcctt ttgtctccga ccatcaggca 1620
cctgagtcgc tgtctttttc gtgacattca gttcgctgcg ctcacggctc tggcagtgaa 1680
tgggggtaaa tggcactaca ggcgcctttt atggattcat gcaaggaaac tacccataat 1740
acaagaaaag cccgtcacgg gcttctcagg gcgttttatg gcgggtctgc tatgtggtgc 1800
tatctgactt tttgctgttc agcagttcct gccctctgat ttccagtct gaccacttcg 1860 gattatcccg tgacaggtca ttcagactgg ctaatgcacc cagtaaggca gcggtatcat 1920
caacaggctt acccgtctta ctgtcaaccg gatct 1955

<210> SEQ ID NO 31
<211> LENGTH: 1686
<212> TYPE: DNA
<213> ORGANISM: Escherichia coli

<400> SEQUENCE: 31
cacttttgtt acccgccaaa caaaacccaa aaacaaccca tacccaaccc aataaaacac 60
caaaacaaga caaataatca ttgattgatg gttgaaatgg ggtaaacttg acaaacaaac 120
ccacttaaaa cccaaaacat acccaaacac acaccaaaaa aacaccataa ggagttttat 180
aaatgttggt attcattgat gacggttcaa caaacatcaa actacagtgg caggaaagcg 240
acggaacaat taaacagcac attagcccga acagcttcaa acgcgagtgg gcagtctctt 300
ttggtgataa aaaggtcttt aactacacac tgaacggcga acagtattca tttgatccaa 360
tcagcccgga tgctgtagtc acaaccaata tcgcatggca atacagcgac gttaatgtcg 420
ttgcagtgca tcacgcctta ctgaccagtg gtctgccggt aagcgaagtg gatattgttt 480
gcacacttcc tctgacagag tattacgaca gaaataacca acccaatacg gaaaatattg 540
agcgtaagaa agcaaacttc cggaaaaaaa ttacattaaa tggcggggat acattcacaa 600
taaaagatgt aaaagtcatg cctgaatcta taccggcagg ttatgaagtt ctacaagaac 660
tggatgagtt agattcttta ttaattatag atctcggggg caccacatta gatatttctc 720
aggtaatggg gaaattatcg gggatcagta aaatatacgg agactcatct cttggtgtct 780
ctctggttac atctgcagta aaagatgccc tttctcttgc gagaacaaaa ggaagtagct 840
atcttgctga cgatataatc attcacagaa aagataataa ctatctgaag caacgaatta 900
atgatgagaa caaaatatca atagtcaccg aagcaatgaa tgaagcactt cgtaaacttg 960
agcaacgtgt attaaatacg ctcaatgaat tttctggtta tactcatgtt atggttatag 1020
gcggtggcgc agaattaata tgcgatgcag taaaaaaaca cacacagatt cgtgatgaac 1080
gtttttttcaa aaccaataac tctcaatatg atttagttaa cggtatgtat ctcataggta 1140
attaatgatg gacaagcgca gaaccattgc cttcaaacta aatccagatg taaatcaaac 1200
agataaaatt gtttgtgata cactggacag tatcccgcaa ggggaacgaa gccgccttaa 1260
ccgggccgca ctgacggcag gtctggcctt atacagacaa gatccccgga ccccttttcct 1320
tttatgtgag ctgctgacga aagaaaccac attttcagat atcgtgaata tattgagatc 1380
gctatttcca aaagagatgg ccgattttaa ttcttcaata gtcactcaat cctcttcaca 1440
acaagagcaa aaaagtgatg aagagaccaa aaaaaatgcg atgaagctaa taaattaatt 1500
caattattat tgagttccct ttatccacta tcaggctgga taaagggaac tcaatcaagt 1560
tattttctta ccagtcatta cataatcgtt attatgaaat aatcgtttgc actgtctctg 1620
ttattcaggc aatttcaata aaggcacttg ctcacgctct gtcattttct gaaactcttc 1680
atgctg 1686

<210> SEQ ID NO 32
<211> LENGTH: 367
<212> TYPE: DNA
<213> ORGANISM: Escherichia coli

<400> SEQUENCE: 32
gacagtaaga cgggtaagcc tgttgatgat accgctgcct tactgggtgc attagccagt 60
ctgaatgacc tgtcacggga taatccgaag tggtcagact ggaaaatcag agggcaggaa 120
ctgctgaaca gcaaaaagtc agatagcacc acatagcaga cccgccataa aacgccctga 180
gaagcccgtg acgggctttt cttgtattat gggtagtttc cttgcatgaa tccataaaag 240
gcgcctgtag tgccatttac ccccattcac tgccagagcc gtgagcgcag cgaactgaat 300
gtcacgaaaa agacagcgac tcaggtgcct gatggtcgga gacaaaagga atattcagcg 360
atttgcc 367

<210> SEQ ID NO 33
<211> LENGTH: 459
<212> TYPE: DNA
<213> ORGANISM: Escherichia coli

<400> SEQUENCE: 33
ttctgtggta gcacagaata atgaaaagtg tgtaaagaag ggtaaaaaaa accgaatgcg 60
aggcatccgg ttgaaatagg ggtaaacaga cattcagaaa tgaatgacgg taataaataa 120
agttaatgat gatagcggga gttattctag ttgcgagtga aggttttgtt ttgacattca 180
gtgctgtcaa atacttaaga ataagttatt gattttaacc ttgaattatt attgcttgat 240
gttaggtgct tatttcgcca ttccgcaata atcttaaaaa gttcccttgc atttacattt 300
tgaaacatct atagcgataa atgaaacatc ttaaaagttt tagtatcata ttcgtgttgg 360
attattctgc atttttgggg agaatggact tgccgactga ttaatgaggg ttaatcagta 420
tgcagtggca taaaaaagca aataaaggca tataacaga 459

<210> SEQ ID NO 34
<211> LENGTH: 734
<212> TYPE: DNA
<213> ORGANISM: Shigella flexneri

<400> SEQUENCE: 34
catatgattg acctgaatga atatacagta ttggaatgca ttatccggag tgttgtgtaa 60
caatgtctgg ccaggtttgt ttcccggaac cgaggtcaca acatagtaaa agcgctattg 120
gtaatggtac aatcgcgcgt ttacacttat tcagaacgac aggagacacg aacatggcca 180
gcagaggcgt aaacaaggtt attctcgttg gtaatctggg tcaggacccg gaagtacgct 240
acatgccaaa tggtggcgca gttgccaaca ttacgctggc tacttccgaa tcctggcgtg 300
ataaagcgac cggcgagatg aaagaacaga ctgaatggca ccgcgttgtg ctgttcggca 360
aactggcaga agtggcgagc gaatatctgc gtaaaggttc tcaggtttat atcgaaggtc 420
agctgcgtac ccgtaaatgg accgatcaat ccggtcagga tcgctacacc acagaagtcg 480
tggtgaacgt tggcggcacc atgcagatgc tgggtggtcg tcagggtggt ggcgctccgg 540
caggtggcaa tatcggtggt ggtcagccgc agggcggttg gggtcagcct cagcagccgc 600
agggtggcaa tcagttcagc ggcggcgcgc agtctcgccc gcagcagtcc gctccggcag 660
cgccgtctaa cgagccgccg atggactttg atgatgacat tccgttctga tttgtcatta 720
aaacaatagc tagc 734

<210> SEQ ID NO 35
<211> LENGTH: 1467
<212> TYPE: DNA
<213> ORGANISM: Salmonella paratyphi

<400> SEQUENCE: 35
atgctacgta tcgctaaaga agccctgacg tttgacgacg tcctccttgt tcccgctcac 60
tccaccgttt tgccgaatac tgccgatctc agcacgcagt tgacgaaaac tattcgtctg 120
aatattccta tgctttctgc ggcgatggac accgtgacgg aagcgcgcct ggcaattgcc 180
ctggcccagg aaggcggcat tggttttatc cacaaaaaca tgtccattga gcgccaggcg 240
gaagaagttc gccgcgtgaa gaaacacgag tccggcgtag tgaccgaccc gcagaccgtc 300
ctgccaacca ccacgttgca tgaagtgaaa gccctgaccg agcgtaacgg ttttgcgggc 360

```
tatccggtgg tgactgaaga taacgagctg gtggggatca tcaccggtcg tgacgtgcgt    420

tttgtgactg acctgaacca gccggtaagt gtctacatga cgccgaaaga gcgtctggtg    480

accgttcgtg aaggcgaagc ccgtgaagtc gtgctggcaa aaatgcacga aaaacgcgta    540

gaaaaagcgc tggtcgttga tgataacttc catctgcttg gcatgattac cgtaaaagat    600

ttccagaaag cggaacgtaa accaaactcc tgtaaagatg agcagggccg tttacgtgtc    660

ggcgcggcgg tcggcgcagg cgcgggcaac gaagagcgcg ttgacgcgct ggtggcggca    720

ggcgttgacg tactgctgat cgactcctct cacggtcact ctgaaggcgt gttgcaacgt    780

atccgtgaga cgcgtgctaa atatcctgac ctgcaaatca tcggcggcaa cgttgcgacg    840

ggcgcaggcg ctcgcgcact ggcggaagcc ggttgcagcg cggtgaaagt gggtatcggc    900

ccgggctcca tctgtaccac tcgtatcgtg actggtgtgg gcgttccgca gatcaccgct    960

gtttccgacg cggtagaagc gctggaaggc accggaattc cggttatcgc tgacggcggt   1020

atccgtttct ccggcgacat cgccaaagcc atcgccgcag gcgcgagcgc cgtgatggtg   1080

ggctctatgc tggccggtac cgaagaatcc ccgggcgaaa tcgaactcta ccagggccgt   1140

tcgtacaaat cttaccgcgg catgggctcg ctgggcgcga tgtccaaagg ttcctccgac   1200

cgttacttcc agagcgacaa cgccgctgac aaactggtgc cggaaggtat cgaaggccgc   1260

gtagcctata aaggtcgcct gaaagagatc attcaccagc agatgggcgg cctgcgctcc   1320

tgtatggggc tgaccggttg tgctaccatc gacgaactgc gtactaaagc ggagtttgtg   1380

cgtatcagcg gtgcgggtat ccaggaaagc cacgttcacg acgtgaccat caccaaagag   1440

tccccgaact accgtctggg ctcctga                                       1467
```

<210> SEQ ID NO 36
<211> LENGTH: 1578
<212> TYPE: DNA
<213> ORGANISM: Salmonella paratyphi

<400> SEQUENCE: 36

```
atgacggaaa acattcataa gcatcgcatc ctcattctgg acttcggttc tcagtacact     60

caactggttg cgcgccgcgt gcgtgagctg ggtgtttact gcgaactgtg ggcgtgggat    120

gtgacagaag cacaaattcg tgacttcaac ccaagcggca ttattctttc cggcggcccg    180

gaaagcacca ccgaagaaaa cagcccgcgc gcgccgcagt atgtctttga agcaggcgtg    240

ccggtatttg gcgtttgcta tggtatgcag accatggcga tgcagcttgg cggtcatgta    300

gaaggttcta atgagcgtga atttggttat gcgcaggtcg aagtgttgac cgacagcgcg    360

ctggttcgcg gtattgaaga ttccctgacc gcagacggca aaccgctgct ggacgtgtgg    420

atgagccacg gcgataaagt gacggcgatt ccgtccgact tcgtgaccgt cgccagcacc    480

gagagctgcc cgttcgccat catggctaac gaagaaaaac gcttctacgg cgtacagttc    540

cacccggaag tgacccacac ccgccagggg atgcgcatgc tggagcgttt tgtgcgtgat    600

atctgccagt gtgaagcgtt gtggacgccg gcgaagatca tcgacgacgc cgtggcgcgc    660

attcgcgagc aggtaggcga cgataaagtg atcctcggtc tctccggcgg cgtggattct    720

tccgtcaccg caatgctgct gcaccgcgcg atcggtaaaa atctgacctg tgtattcgtc    780

gacaacggcc tgctgcgtct caacgaagcc gagcaggtga tggacatgtt tggcgaccat    840

tttggcctga atatcgttca cgttccggcg gaagagcgct tcctgtccgc gttggctggc    900

gaaaacgatc cggaagcgaa gcgtaagatc attggccgtg tttttgtgga agtgttcgac    960

gaagaagcgt tgaaactgga agacgtgaaa tggctggcgc agggcaccat ctaccctgac   1020
```

```
gtcatcgagt ctgcggcgtc tgcaaccggt aaagcgcacg tcatcaaatc tcaccacaat   1080

gttggcggcc tgccgaaaga gatgaagatg ggctggttg aaccgctgaa agagctgttc   1140

aaagacgaag tgcgtaagat tggtctggag ctgggcctgc cgtacgacat gctgtaccgt   1200

catccgttcc cggggccggg cctcggcgta cgtgtactgg gtgaagtgaa gaaagagtac   1260

tgcgacctgt tgcgccgtgc tgacgccatc ttcattgaag agctgcgtaa ggcggatctg   1320

tacgacaaag tcagccaggc gttcaccgtc ttcctgccag tacgctccgt tggcgtaatg   1380

ggcgatggtc gtaagtacga ttgggtggtc tccctgcgtg ctgtcgaaac catcgacttt   1440

atgactgcgc actgggcgca tctgccgtat gacttcctgg gtcgtgtttc caaccgcatc   1500

atcaatgaag tcaacgggat ttcccgtgtg gtgtatgaca tcagcggtaa accaccggct   1560

accattgagt gggaataa                                                 1578
```

<210> SEQ ID NO 37
<211> LENGTH: 624
<212> TYPE: DNA
<213> ORGANISM: Salmonella paratyphi

<400> SEQUENCE: 37

```
atgtcataca gcggagaacg agataatttg gcccctcata tggcgctggt gccgatggtc     60

attgaacaga cctcacgcgg tgagcgctct tttgatatct attctcgtct acttaaggaa    120

cgcgtcatat ttctgaccgg ccaggtcgaa gaccatatgg ctaacctgat cgtggcgcag    180

atgctgttcc tggaagcgga aaacccggaa aaagatatct atctgtacat taattctcct    240

ggcggcgtaa ttactgcggg gatctccatc tatgacacca tgcagtttat taagccagac    300

gtcagcacca tttgtatggg acaggcggcc tctatggggg cgtttctgct gactgccggg    360

gcgaaaggca aacgtttctg cttgccgaac tctcgcgtca tgatccacca gccgctgggc    420

ggctaccagg gccaggcgac ggatattgaa attcacgccc gcgaaatttt gaaagtaaaa    480

gggcgcatga atgaacttat ggcgcatcat acgggtcaat ctcttgagca gattgaacgt    540

gatactgagc gcgatcgctt cctctccgcg cctgaagcgg tagagtacgg tttggttgac    600

tcaattttga cccatcgtaa ttga                                           624
```

<210> SEQ ID NO 38
<211> LENGTH: 1272
<212> TYPE: DNA
<213> ORGANISM: Salmonella paratyphi

<400> SEQUENCE: 38

```
atgacagata aacgcaaaga tggctcgggc aaattgttgt actgctcttt ttgcggcaaa     60

agccagcatg aagtgcgcaa gctgattgcc ggtccatccg tgtatatctg cgacgaatgc    120

gtcgatttat gtaacgacat tattcgcgaa gaaattaaag aagttgctcc gcaccgtgaa    180

cgtagtgcgc tgccgacgcc gcatgaaatt cgtacccacc tggacgatta cgttatcggc    240

caggagcagg cgaaaaaagt gctggcggtg gcggtctata accactacaa gcgtctgcgt    300

aacggtgata ccagcaatgg cgtcgagtta ggcaaaagca acattctgct gattggaccg    360

accggttccg gtaaaacgct gctggcggaa acgctggcgc gcttgctgga tgtgccgttc    420

actatggcgg atgcgaccac gctgaccgaa gcgggttacg tgggtgaaga cgtcgagaat    480

atcattcaga aactgttgca gaaatgcgac tacgacgtgc aaaaagcgca gcgtgggatt    540

gtctacattg atgaaatcga taagatttcg cgtaaatcag acaatccgtc cattacccgc    600

gatgtttccg gcgaaggcgt acagcaggcg ttgctgaaac tgatcgaagg caccgtcgcc    660
```

gcggttccac cgcagggcgg tcgcaaacat ccgcagcagg agttcttaca ggtagatacc 720
tctaagattc tgtttatctg cggcggcgcg tttgctggtc tggataaagt gatcgctaac 780
cgtgttgaaa ccggctccgg cattggtttt ggcgcgacgg tgaaagcgaa gtccgacaaa 840
gccagcgaag gcgagctgtt gtcgcaggtt gaaccggaag atttgatcaa atttggtctg 900
attcctgagt ttatcggtcg tctgccagtg gtggcgacgc tgaacgaact cagcgaagaa 960
gcgctgattc aaatcctgaa agagccgaaa aatgcgctga ccaagcagta tcaggcgctg 1020
tttaacctgg aaggcgtcga tctggaattc cgtgacgaag cgctggacgc tatcgccagg 1080
aaagcaatgg cgcgtaaaac cggtgcccgt ggtctgcgtt ctatcgtcga agcggcgctg 1140
ctggatacca tgtacgattt gccatctatg gaagacgtcg aaaaagtggt gatcgacgag 1200
tccgttattg ccggtcagag taagccgttg ctgatttacg gcaaaccgga agcgcaggct 1260
tctggcgaat aa 1272

<210> SEQ ID NO 39
<211> LENGTH: 1272
<212> TYPE: DNA
<213> ORGANISM: Salmonella typhi

<400> SEQUENCE: 39
atgacagata aacgcaaaga tggctcgggc aaattgttgt actgctcttt ttgcggcaaa 60
agccagcatg aagtgcgcaa gctgattgcc ggtccatccg tgtatatctg cgacgaatgc 120
gtcgatttat gtaacgacat tattcgcgaa gaaattaaag aagttgctcc gcaccgtgaa 180
cgtagtgcgc tgccgacgcc gcatgaaatt cgtactcacc tggacgatta cgttatcggc 240
caggagcagg cgaaaaaagt gctggcggtg gcggtctata accactacaa gcgtctgcgt 300
aacggcgata ccagcaatgg cgtcgagtta ggcaaaagca acattctgct gactggaccg 360
accggttccg gtaaaacgct gctggcggaa acgctggcgc gcttgctgga tgtgccgttc 420
actatggcgg atgcgaccac gctgaccgaa gcgggttacg tgggggaaga cgtcgagaat 480
atcattcaga aactgttgca gaaatgcgac tacgacgtgc aaaaagcgca gcgtgggatt 540
gtctacattg atgaaatcga taagatttcg cgtaaatcag acaatccgtc cattacccgc 600
gatgtttccg gcgaaggcgt acagcaggcg ttgctgaaac tgatcgaagg caccgtcgcc 660
gcggttccac cgcagggcgg tcgcaaacat ccgcagcagg agttcttaca ggtagatacc 720
tctaagattc tgtttatctg cggcggcgcg tttgccggtc tggataaagt gatcgctaac 780
cgtgttgaaa ccggctccgg cattggtttt ggcgcgacgg tgaaagcgaa gtccgacaaa 840
gccagtgaag gcgagctgtt gtcgcaggtt gaaccggaag atttgatcaa atttggtctg 900
attcctgagt ttatcggtcg tctgccagtg gtggcgacgc tgaacgaact cagcgaagaa 960
gcgctggttc aaatcctgaa agagccgaaa aatgcgctga ccaagcagta tcaggcgctg 1020
tttaacctgg aaggcgtcga tctggaattc cgtgacgaag cgctgaacgc tatcgccagg 1080
aaagcgatgg cgcgtaaaac tggtgcccgt ggcctgcgtt ctatcgtcga agcggcgctg 1140
ctggatacca tgtacgattt gccatctatg gaagacgtcg aaaaagtggt gattgacgag 1200
tccgttattg ccggtcagag taagccgttg ctgatttacg gcaaaccgga agcgcaggct 1260
tctggcgaat aa 1272

<210> SEQ ID NO 40
<211> LENGTH: 624
<212> TYPE: DNA
<213> ORGANISM: Salmonella typhi -continued

<400> SEQUENCE: 40

```
atgtcataca gcggagaacg agataatttg gcccctcata tggcgctggt gccgatggtc     60
attgaacaga cctcacgcgg tgagcgctct tttgatatct attctcgtct acttaaggaa    120
cgcgtcatat ttctgaccgg ccaggtcgaa gaccatatgg ctaacctgat cgtggcgcag    180
atgctgttcc tggaagcgga aaacccggaa aaagatatct atctgtacat taattctcct    240
ggcggcgtaa ttactgcggg gatgtccatc tatgacacca tgcagtttat taagccagac    300
gtcagcacca tttgtatggg acaggcggcc tctatggggg cgtttctgct gactgccggg    360
gcgaaaggca aacgtttctg cttgccgaac tctcgcgtca tgatccacca gccgctgggc    420
ggctatcagg gccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600
tcaattttga cccatcgtaa ttga                                           624
```

ATTENUATED *SALMONELLA ENTERICA* SEROVAR PARATYPHI A AND USES THEREOF

RELATED APPLICATIONS

The present application claims benefit of U.S. Provisional Application No. 60/731,349, filed Oct. 28, 2005, incorporated herein in its entirety.

BACKGROUND OF THE INVENTION

Enteric fever caused by members of the genus *Salmonella*, including typhoid and paratyphoid fevers, continues to constitute a significant disease and mortality burden among populations in developing countries (Lancet 2005; 366:749-762) and represents a notable risk for travelers (Lancet Infect Dis. 2005; 5(10):623-628). Incidences of enteric fever caused by *Salmonella enterica serovars Typhi* and *Paratyphi* A (*S. Typhi* and *S. Paratyphi* A) are on the rise due to the emergence and spread of antibiotic resistant variants (Lancet Infect Dis. 2005 5(10):623-8). Although the clinical disease caused by *S. Paratyphi* A is overall somewhat milder than that due to *S. Typhi*, the former can nevertheless result in full-blown enteric fever with an assortment of complications and, if untreated or improperly treated, can result in death. A need exists for vaccines that are safe and effective in combating *Salmonella* infections.

SUMMARY OF THE INVENTION

The present invention is drawn to an attenuated *S. Paratyphi* A strain, preferably a live, attenuated *S. Paratyphi* A strain.

In one embodiment, the *S. Paratyphi* A strains of the present invention have at least one attenuating mutation selected from the group consisting of attenuating mutations in the guaBA loci, the guaB gene, the guaA gene, the clpP gene and the clpX gene. In preferred embodiments, the *S. Paratyphi* A strain has an attenuating mutation in the guaB gene, the guaA gene and the clpP gene. In another preferred embodiment, the *Salmonella Paratyphi* A strain has an attenuating mutation in the guaB gene, the guaA gene and the clpX gene. In a further preferred embodiment, the *Salmonella Paratyphi* A strain has an attenuating mutation in the guaB gene, the guaA gene, the clpP gene and the clpX gene.

In one embodiment the attenuating mutations of the guaBA loci, the guaB gene, the guaA gene, the clpP gene, and the clpX gene are attenuating mutations that reduce the level of expression the loci or the genes, or that block expression of the loci or the genes.

In another embodiment the attenuating mutations of the guaBA loci, the guaB gene, the guaA gene, the clpP gene, and the clpX gene are attenuating mutations that reduce the activity of a polypeptide encoded by the loci or the genes, or inactivates a polypeptide encoded by the loci or the genes.

In a preferred embodiment, the *Salmonella Paratyphi* A strain is the *S. Paratyphi* A 9150 strain.

The present invention also includes *S. Paratyphi* A strains that have at least one attenuating mutation selected from the group consisting of an attenuating mutation in the guaBA loci, the guaB gene, the guaA gene, the clpP gene and the clpX gene, and that further comprises a stabilized plasmid expression system.

In a preferred embodiment, the stabilized plasmid expression system comprises an expression vector having (a) a restricted-copy-number origin of replication cassette, (b) at least one post-segregational killing cassette, (c) at least one partitioning cassette, and (d) an expression cassette.

In preferred embodiments, the restricted-copy-number origin of replication cassette comprises (i) a nucleotide sequence encoding an origin of replication that limits the expression vector to an average plasmid copy number of about 2 to 75 copies per cell, (ii) a first unique restriction enzyme cleavage site located 5' of the nucleotide sequence encoding the origin of replication, and (iii) a second unique restriction enzyme cleavage site located 3' of the nucleotide sequence encoding the origin of replication.

In the same embodiments, the post-segregational killing cassette comprises (i) a nucleotide sequence encoding at least one post-segregational killing locus, (ii) a third unique restriction enzyme cleavage site located 5' of the nucleotide sequence encoding the post-segregational killing locus, and (iii) a fourth unique restriction enzyme cleavage site located 3' of the nucleotide sequence encoding the post-segregational killing locus.

In the same embodiments, the partitioning cassette comprises (i) a nucleotide sequence encoding at least one partitioning function, (ii) a fifth unique restriction enzyme cleavage site 5' of the nucleotide sequence encoding the partitioning function, and (iii) a sixth unique restriction enzyme cleavage site located 3' of the nucleotide sequence encoding the partitioning function.

In the same embodiments, the expression cassette comprises (i) a nucleotide sequence encoding a selected antigen operably linked to a promoter, (ii) a seventh unique restriction enzyme cleavage site located 5' of the nucleotide sequence encoding the selected antigen operably linked to a promoter, and (iii) an eighth unique restriction enzyme cleavage site located 3' of the nucleotide sequence encoding the selected antigen operably linked to a promoter.

In preferred embodiments, the nucleotide sequence encoding the origin of replication is a nucleotide sequence selected from the group consisting of the oriE1 sequence of SEQ ID NO: 28, the ori101 sequence of SEQ ID NO: 30, and the ori15A sequence of SEQ ID NO: 29.

In preferred embodiments, the nucleotide sequence encoding the post-segregational killing locus is a nucleotide sequence selected from the group consisting of a nucleotide sequence encoding the ssb balanced-lethal system, a nucleotide sequence encoding the asd balanced-lethal system, a nucleotide sequence encoding the phd-doc proteic system, and a nucleotide sequence encoding the hok-sok antisense system. More preferably, the post-segregational killing locus is a nucleotide sequence encoding ssb balanced-lethal system selected from the group consisting of the *Shigella flexneri* ssb locus, the *Salmonella Typhi* ssb locus, and the *E. coli* ssb locus. Even more preferably, the ssb balanced-lethal system is a ssb locus comprising a ssb inducible promoter, a ssb constitutive promoter and a ssb coding region of *S. flexneri* 2a strain CVD 1208s set forth in SEQ ID NO: 34.

In preferred embodiments, the nucleotide sequence encoding the partitioning function is a nucleotide sequence selected from the group consisting of the *E. coli* parA locus set forth in SEQ ID NO: 31 and the *E. coli* pSC101 par locus set forth in SEQ ID NO: 32.

In preferred embodiments, the promoter is an inducible promoter, more preferably an ompC promoter, even more preferably the ompC promoter set forth in SEQ ID NO: 33.

In one embodiment, the nucleotide sequence encoding a selected antigen is a nucleotide sequence encoding a homologous antigen. In another embodiment, the nucleotide sequence encoding a selected antigen is a nucleotide sequence encoding a heterologous antigen.

In preferred embodiments, the nucleotide sequence encoding a selected antigen is a nucleotide sequence encoding a heterologous antigen selected from the group consisting of a viral antigen, a bacterial antigen, a cancer antigen, and an auto-immune antigen.

The present invention also includes a pharmaceutical formulation comprising one or more of the attenuated *Salmonella Paratyphi* A strains of the present invention. Preferably the pharmaceutical formulations are oral pharmaceutical formulations.

The present invention further includes a method of inducing an immune response in a subject, comprising administering an immunologically-effective amount of a pharmaceutical formulation of the present invention to a subject. Preferably, the immune response is a protective immune response.

The immunologically-effective amount of the pharmaceutical formulation contains about $10^2$ cfu to about $10^{10}$ cfu, more preferably about $10^6$ cfu to about $10^9$ cfu, of the attenuated *S. Paratyphi* A strain within the pharmaceutical formulation.

In one embodiment, the immune response is to *Salmonella Paratyphi* A. In another embodiment, the immune response is to the selected antigen. In a further embodiment, the immune response is to both *Salmonella Paratyphi* A and the selected antigen.

The Lambda Red-mediated mutagenesis system may be used to mutate or delete various chromosomal loci and genes from the *S. Paratyphi* strains of the present invention.

DETAILED DESCRIPTION OF THE INVENTION

A. Attenuated *S. Paratyphi* A Strains

Figure 1:
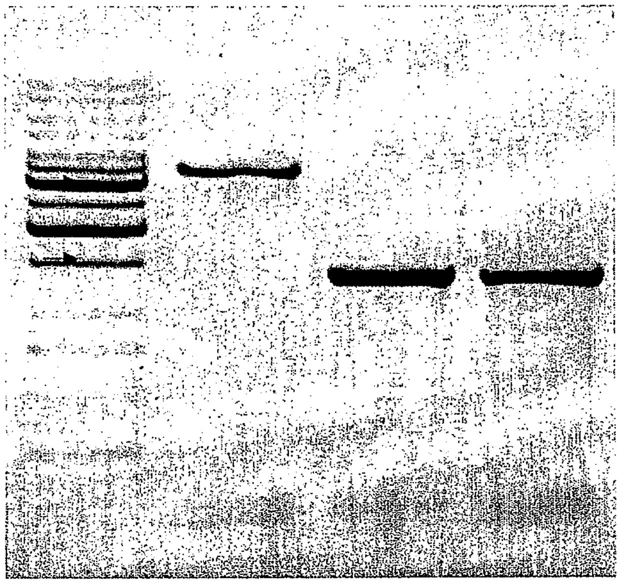
FIG. 1 shows the PCR amplification products of guaBA and guaBA::cml. Lane 1 is wild-type guaBA; lanes 2 and 3 are guaBA::cml. Arrows indicate molecular weight marker bands of 3 kb (top) and 1.5 kb (bottom).

The present invention relates to an attenuated *S. Paratyphi* A strain. Such attenuated *S. Paratyphi* A strains may be used to induce an immune response in a subject without causing disease in the subject.

The *S. Paratyphi* A strain used as the starting material of the present invention may be any *S. Paratyphi* A strain and the identity of the strain is not critical. Preferred *S. Paratyphi* A strains include *S. Paratyphi* A 9150 strain.

The *S. Paratyphi* A strains of the present invention are attenuated. As used herein, attenuated strains of *S. Paratyphi* A are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics. The attenuated strains of the present invention may be living or dead.

In addition to the attenuated *S. Paratyphi* A strains of the present invention, attenuated strains of other enteric pathogens (e.g., *Salmonella Typhi, Salmonella Paratyphi* B, *Shigella, Vibrio cholerae*), commensals (e.g., *Lactobacillus, Streptococcus gordonii*) and licensed vaccine strains (e.g., BCG) are also encompassed within the scope of the invention. These additional strains have all of the attenuating mutations of the *S. Paratyphi* A strains of the present invention, may be transformed with the stabilized plasmid expression system of the present invention, and may be used as an immunizing composition as described herein.

In preferred embodiments, the attenuated *S. Paratyphi* A strains of the present invention have a mutation in one or more of the guaBA loci, the guaB gene, the guaA gene, the clpP gene and the clpX gene of *S. Paratyphi*. For example, the attenuated *S. Paratyphi* A strains of the present invention may have a mutation (i) in the guaB gene and the clpP gene, (ii) in the guaA gene and the clpP gene, (iii) in the guaB gene, the guaA gene, and the clpP gene, (iv) in the guaBA loci and the clpP gene, (v) in the guaB gene and the clpX gene, (vi) in the guaA gene and the clpX gene, (vii) in the guaB gene, the guaA gene, and the clpX gene, (viii) in the guaBA loci and the clpX gene, (ix) in the guaB gene, the clpP gene and the clpX gene, (x) in the guaA gene, the clpP gene and the clpX gene, (xi) in the guaB gene, the guaA gene, the clpP gene and the clpX gene, or (xii) in the guaBA loci, the clpP gene and the clpX gene.

The mutations of the loci and genes described herein may be any mutation, such as one or more nucleic acid deletions, insertions or substitutions. The mutations may be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes.

Preferably, in the present invention, the chromosomal genome of the *S. Paratyphi* A strain is modified by removing or otherwise modifying the guaBA loci, and thus blocking the de novo biosynthesis of guanine nucleotides. More preferably, a mutation in the guaBA loci inactivates the purine metabolic pathway enzymes IMP dehydrogenase (encoded by guaB) and GMP synthetase (encoded by guaA). As a consequence of these mutations, *S. Paratyphi* A are unable to de novo synthesize GMP, and consequently GDP and GTP nucleotides, which severely limits bacterial growth in mammalian tissues. In vitro, the ΔguaBA *S. Paratyphi* A mutants of the present invention are unable to grow in minimal medium unless supplemented with guanine. In tissue culture, the ΔguaBA *S. Paratyphi* A mutants of the present invention were found to show a significant reduction in their capability for invasion. ΔguaBA *S. Paratyphi* A mutants may scavenge guanine nucleotides from the tissues of the mammalian host. However, their assimilation into *S. Paratyphi* A requires prior dephosphorylation to nucleosides by periplasmic nucleotidases to be incorporated as nucleotide precursors into the guanine salvage pathway. Therefore, as nucleotides are readily available in the intracellular environment of the mammalian host, the attenuation due to the de novo synthesis of guanine nucleotides is due either to the inefficiency of the salvage pathway or to reasons that are obscure to today's knowledge.

The guaA gene of *S. Paratyphi* A 9150, which encodes GMP synthetase, is 1578 bp in size (SEQ ID NO: 36), and is 98% homologous to the guaA gene of *S. Typhi* Ty2 as determined by NCBI BLAST nucleotide comparison. Deletion mutants can be produced by eliminating portions of the coding region of the guaA gene of *S. Paratyphi* A so that proper folding or activity of GuaA is prevented. For example, about 25 to about 1500 bp, about 75 to about 1400 bp, about 100 to about 1300 bp, or all of the coding region can be deleted. Alternatively, the deletion mutants can be produced by eliminating, for example, a 1 to 100 bp fragment of the guaA gene of *S. Paratyphi* Aso that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the guaA gene, i.e., deletions in the elements controlling translation of the guaA gene, such as in a ribosome binding site.

The guaB gene of *S. Paratyphi* A 9150, which encodes IMP dehydrogenase, is 1467 bp in size (SEQ ID NO: 35), and is 98% homologous to the guaB gene of *S. Typhi* Ty2 as determined by NCBI BLAST nucleotide comparison. Deletion mutants can be produced by eliminating portions of the coding region of the guaB gene of *S. Paratyphi* A so that proper folding or activity of GuaB is prevented. For example, about 25 to about 1400 bp, about 75 to about 1300 bp, about 100 to about 1200 bp, or all of the coding region can be deleted. Alternatively, the deletion mutants can be produced by eliminating, for example, a 1 to 100 bp fragment of the guaB gene of *S. Paratyphi* A so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the guaB gene, i.e., deletions in the elements controlling transcription of the guaB gene, such as in a promoter.

The clpP gene of *S. Paratyphi* A 9150, which encodes a serine-protease, is 624 bp in size (SEQ ID NO: 37), and 99% homologous to the clpP gene of *S. Typhi* Ty2 as determined by NCBI BLAST nucleotide comparison. Deletion mutants can be produced by eliminating portions of the coding region of the clpP gene of *S. Paratyphi* A so that proper folding or activity of ClpP is prevented. For example, about 25 to about 600 bp, about 75 to about 500 bp, about 100 to about 400 bp, or all of the coding region can be deleted. Alternatively, the deletion mutants can be produced by eliminating, for example, a 1 to 100 bp fragment of the clpP gene of *S. Paratyphi* A so that the proper reading frame of the gene is shifted. In the latter instance, a nonsense polypeptide may be produced or polypeptide synthesis may be aborted due to a frame-shift-induced stop codon. The preferred size of the deletion is about 25 to 600 bp. Deletions can also be made that extend beyond the clpP gene, i.e., deletions in the elements controlling transcription of the clpP gene, such as in a promoter.

The clpX gene of *S. Paratyphi* A 9150, which encodes a chaperone ATPase, is 1272 bp in size (SEQ ID NO: 38), and 99% homologous to the clpX gene of *S. Typhi* Ty2 as determined by NCBI BLAST nucleotide comparison. Deletion mutants can be produced by eliminating portions of the coding region of the clpX gene of *S. Paratyphi* A so that proper folding or activity of ClpX is prevented. For example, about 25 to about 1200 bp, about 75 to about 1100 bp, about 100 to about 1000 bp, or all of the coding region can be deleted. Alternatively, the deletion mutants can be produced by eliminating, for example, a 1 to 100 bp fragment of the clpX gene of *S. Paratyphi* A so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the clpX gene, i.e., deletions in the elements controlling transcription of the clpX gene, such as in a promoter.

Deletions can be made in any of the loci or genes included herein by using convenient restriction sites located within the loci or genes, or by site-directed mutagenesis with oligonucleotides (Sambrook et al, In: Molecular Cloning, A Laboratory Manual, Eds., Cold Spring Harbor Publications (1989)).

Inactivation of the loci or genes can also be carried out by an insertion of foreign DNA using any convenient restriction site, or by site-directed mutagenesis with oligonucleotides (Sambrook et al, supra) so as to interrupt the correct transcription of the loci or genes. The typical size of an insertion that can inactivate the loci or genes is from 1 base pair to 100 kbp, although insertions smaller than 100 kbp are preferable. The insertion can be made anywhere inside the loci or gene coding regions or between the coding regions and the promoters.

Other methods for the inactivation of the loci and genes include the transfer into *Salmonella* of deletions or insertions made in other enterobacteriae guaBA loci, guaA, guaB, clpP or clpX genes, transposon-generated deletions, and imprecise excision of DNA insertions.

Preferably, the bacterial loci and genes are mutated using Lambda Red-mediated mutagenesis (Datsenko and Wanner, *PNAS USA* 97:6640-6645 (2000)). Briefly, in step 1 host bacteria targeted for mutation are transformed with a temperature sensitive plasmid encoding λ Red recombinase. These bacteria are grown in the presence of arabinose to induce λ Red production. Chromosomal mutagenesis of a target sequence is accomplished by electroporation of the host with linear DNA in which the target gene is replaced with an antibiotic resistance marker. This DNA also encodes short regions of flanking chromosomal sequences to allow for chromosomal integration of the resistance marker by λ Red-mediated homologous recombination. Recombinants are selected for on solid media containing the appropriate antibiotic, and incubated at a temperature facilitating the loss of the plasmid encoding λ Red recombinase. For step 2, removal of the chromosomal resistance marker is facilitated by transforming the bacteria with a temperature sensitive plasmid encoding FLP recombinase, which targets unique sequences within the antibiotic resistance marker now present in the host chromosome. Transformants are grown at temperatures permissive for the presence of the FLP recombinase which is expressed constitutively. Mutants are screened via PCR, grown at a temperature to facilitate loss of the plasmid encoding FLP recombinase, and selected for storage.

The attenuated *S. Paratyphi* A strains of the present invention may contain mutations in one or more additional genes. While an extensive discussion of additional attenuating mutations of *Salmonella* spp. is provide in U.S. Pat. No. 6,682,729, exemplary genes include those encoding various biochemical pathways, global regulatory systems, heat shock proteins, other regulatory genes, and putative virulence properties. Specific examples of such attenuating mutations include, but are not limited to: (i) auxotrophic mutations, such as aro, gua, nad, thy, and asd mutations; (ii) mutations that inactivate global regulatory functions, such as cya, crp, phoP/phoQ, $phoP^c$ and ompR mutations; (iii) mutations that modify the stress response, such as recA, htrA, htpR, hsp and groEL mutations; (iv) mutations in specific virulence factors, such as pag and prg (v) mutations that affect DNA topology, such as topA mutations; (vi) mutations that block biogenesis of surface polysaccharides, such as rfb, galE and via mutations; (vii) mutations that modify suicide systems, such as sacB, nuc, hok, gef, kil, and phlA mutations; (viii) mutations that introduce suicide systems, such as lysogens encoded by P22, λ murein transglycosylase and S-gene; and (ix) mutations that disrupt or modify the correct cell cycle, such as minB mutations.

B. Stabilized Expression Plasmid System

The attenuated *S. Paratyphi* A strains of the present invention include those strains engineered to express selected polypeptides (antigens). Such attenuated *S. Paratyphi* A strains can be used to induce an immune response to *S. Paratyphi* itself, or to induce an immune response to the selected antigens expressed by the attenuated *S. Paratyphi* A strains, or both.

Such attenuated *S. Paratyphi* A strains are transformed with a stabilized expression plasmid system. The stabilized expression plasmid system encodes a selected antigen.

The stabilized expression plasmid system comprises expression vector that comprises a plasmid maintenance system (PMS) and a nucleotide sequence encoding a selected antigen.

The stabilized expression plasmid system optimizes the maintenance of the expression vector in the bacteria at two independent levels by: (1) removing sole dependence on balanced lethal maintenance systems; and (2) incorporating a plasmid partition system to prevent random segregation of expression vectors, thereby enhancing their inheritance and stability.

The PMS includes (a) an origin of replication, (b) at least one post-segregational killing function, and (c) at least one partitioning function. Each of the noted elements of the PMS may be an individual cassette of the stabilized expression plasmid system. Each of the cassettes may comprise unique restriction enzyme cleavage sites located at the 5' and 3' ends of the cassettes.

Preferred stabilized expression plasmid systems are those described in pending U.S. patent application Ser. No. 11/542,264, which is incorporated by reference herein in its entirety.

1. Origin of Replication

The PMS includes a restricted-copy-number origin of replication that limits the expression vector to a range of plasmid copies per cell. Due to varying degrees of toxicity associated with different selected antigens (e.g., higher toxicity for antigens derived from parasitic organisms such *Plasmodium falciparum* versus virtually no toxicity for the fragment of tetanus toxin), the stabilized expression plasmid system of the present invention is based on either a low or medium copy number expression vector (plasmid). It will be appreciated by one skilled in the art that the selection of an origin of replication will depend on the degree of toxicity, i.e., the copy number should go down as toxicity to the bacterial strain goes up.

It is preferable for the origin of replication to confer an average copy number which is between about 2 and about 75 copies per cell, between about 5 and about 60 copies per cell, between about 5 to about 30 copies per cell, or between about 5 to about 15 copies per cell. The origins of replication included herein are derived from the *E. coli* plasmid pAT153 (oriE1, ~60 copies per chromosomal equivalent), the *E. coli* plasmid pACYC184 (ori15A, ~15 copies per chromosomal equivalent), and the *Salmonella typhimurium* plasmid pSC101 (ori101, ~5 copies per chromosomal equivalent). The structural organization of the engineered origins of replication cassettes for pSC101, pACYC184, and pAT153 are analogous in structure and function.

The origins of replication of the present invention includes both naturally-occurring origins of replication, as well as origins of replication encoded by nucleotide sequences which are substantially homologous to nucleotide sequences encoding naturally-occurring origins of replication, and which retain the function exhibited by the naturally-occurring origins of replication.

In preferred embodiments, the nucleotide sequence encoding the origin of replication is a nucleotide sequence selected from the group consisting of the oriE1 sequence of SEQ ID NO: 28, the ori101 sequence of SEQ ID NO: 30, and the ori15A sequence of SEQ ID NO: 29.

In a further preferred embodiment, the origin of replication is the oriE1 locus from pSC101, conferring a copy number of approximately 5 copies per genome equivalent, set forth in SEQ ID NO: 28.

2. Partitioning Function

The PMS also includes a partitioning function, also known in the art and herein as a "segregating system" and a "partitioning system." The partitioning function is any plasmid stability-enhancing function that operates to increase the frequency of successful delivery of a plasmid to each newly divided bacterial cell, as compared to the frequency of delivery of a corresponding plasmid without such a function. Partitioning systems include, for example, equi-partitioning systems, pair-site partitioning systems, and the systems provided in Table 1 of chapter 5, Partition Systems of Bacterial Plasmids. B. E. Funnell and R. A. Slavcev. In Plasmid Biology. 2004. B E Funnell and G J Phillips, eds. ASM Press, Washington, D.C.

The partitioning systems of the present invention includes both naturally-occurring partitioning systems, as well as partitioning systems encoded by nucleotide sequences which are substantially homologous to nucleotide sequences encoding naturally-occurring partitioning systems, and which retain the function exhibited by the naturally-occurring partitioning systems.

Exemplary partitioning functions include, without limitation, systems of pSC101, the F factor, the P1 prophage, and IncFII drug resistance plasmids.

In particular, the par passive partitioning locus can be used. The function of the par locus appears to be related to increasing plasmid supercoiling at the origin of replication, which is also the binding site for DNA gyrase. An exemplary par sequence is that of *E. coli*, set forth in SEQ ID NO: 32 (Miller et al. Nucleotide sequence of the partition locus of *Escherichia coli* plasmid pSC101, *Gene* 24:309-15 (1983); GenBank accession no. X01654, nucleotides 4524-4890)).

The active partitioning parA locus may also be used. An exemplary parA locus sequence is set forth in SEQ ID NO: 31.

3. Post-Segregational Killing Function

The PMS further includes at least one post-segregational killing (PSK) function. The PSK function is a function which results in the death of any newly divided bacterial cell which does not inherit the plasmid of interest, and specifically includes balanced-lethal systems such as asd or ssb, proteic systems such as phd-doc, and antisense systems such as hok-sok.

The PSK function of the present invention includes both naturally-occurring PSK functions, as well as PSK functions encoded by nucleotide sequences which are substantially homologous to nucleotide sequences encoding naturally-occurring PSK functions, and which retain the function exhibited by the naturally-occurring PSK functions.

In preferred embodiments, the PSK function is the ssb balanced lethal system. The single-stranded binding protein (SSB) from *S. Typhi* is used to trans-complement an otherwise lethal mutation introduced into the chromosomal ssb gene. The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference).

In the *S. Paratyphi* A strains of the present invention comprising a stabilized expression plasmid system wherein the PSK function is the ssb balanced lethal system, the native ssb locus of the bacteria is inactivated. The native ssb locus may be inactivated by any means known in the art, such as a suicide vector comprising a temperature sensitive origin of replication or Lambda Red-mediated mutagenesis (Datsenko and Wanner, *PNAS USA* 97:6640-6645 (2000)). In a preferred aspect, Lambda Red-mediated mutagenesis is used to inactivate the ssb locus of the attenuated *S. Paratyphi* A strains of the present invention.

In another aspect of the invention, the PSK function is the ssb locus where both the inducible and the constitutive ssb gene promoters are used as the promoters of the ssb PSK function. In a preferred embodiment, the PSK function comprises a ssb inducible promoter, a ssb constitutive promoter and a ssb coding region. Preferably, the ssb locus is the ssb locus of any one of *Shigello flexneri, Salmonella Typhi* and *E. coli*. In one embodiment the ssb locus is the ssb locus of *S. flexneri* 2a strain CVD 1208s set forth in SEQ ID NO: 34.

In a related aspect of the invention, mutated alleles such as ssb-1 (or any mutation functionally equivalent to this allele, such as W54S; Carlini et al. *Mol. Microbiol.* 10:1067-1075 (1993)) may be incorporated into the stabilized expression plasmid system to enhance higher copy number plasmids by over-expression of SSB1-like proteins to form the required biologically active tetramers of SSB.

In a further embodiment, the PMS comprises two PSK functions.

4. Selected Antigen

The stabilized expression plasmid system also comprises a polynucleotide encoding selected antigen under control of a promoter.

The promoter is preferably an environmentally regulatable promoter, controlled by a biologically relevant signal such as osmolarity. In a preferred embodiment, the promoter is the ompC promoter. The ompC gene encodes a porin protein which inserts as a trimer into the outer membrane of a bacterial cell. Expression and control of ompC has been reviewed in considerable detail in Pratt et al., *Molecular Microbiology* 20:911, 1996 and Egger et al., Genes to Cells 2:167, 1997. In a preferred embodiment the ompC promoter fragment from *E. coli is set forth in SEQ ID NO:* 33. See U.S. Pat. No. 6,703,233, which is incorporated herein by reference in its entirety. Transcription of this cassette may be terminated in the 3'-distal region by a trpA transcriptional terminator.

In one aspect, the inducible promoter is the mutated $P_{ompC1}$, or the $P_{ompC3}$ promoter. The promoter may be used to exclusively control the transcription of the downstream selected antigen.

The invention encompasses the expression of any antigen which does not destroy the attenuated *S. Paratyphi* A strain expressing it, and which elicits an immune response when the attenuated *S. Paratyphi* A strain expressing the antigen is administered to the subject. The selected antigens may be homologous (from *S. Paratyphi* A) or heterologous.

Non-limiting examples of the selected antigen include: Shiga toxin 1 (Stx1) antigen, Shiga toxin 2 (Stx2) antigen, hepatitis B, *Haemophilus influenzae* type b, hepatitis A, acellular pertussis ($_{ac}$P), varicella, rotavirus, *Streptococcus pneumoniae* (pneumococcal), and *Neisseria meningitidis* (meningococcal). See Ellis et al., *Advances in Pharm.,* 39: 393423, 1997 (incorporated herein by reference). Where the antigen is a Shiga toxin 2 antigen, the Shiga toxin 2 antigen can, for example, be either a B subunit pentamer or a genetically detoxified Stx 2. Further antigens of relevance to biodefense include: 1) one or more domains of the anthrax toxin Protective Antigen PA83 moiety, including but not limited to domain 4 (the eukaryotic cell-binding domain; D4), the processed 63 kDa biologically active form of PA83, or full-length PA83; and 2) *Clostridium botulinum* antigens comprising the eukaryotic cell-binding heavy chain fragment of any neurotoxin serotype A, B, C, D, E, F, or G, in any combination. Other selected antigens include each of those disclosed in U.S. Pat. No. 6,190,669, incorporated herein by reference.

In one aspect, the selected antigen is an antigen that induced an immune response to cancer. In another aspect, the selected antigen is designed to provoke an immune response to autoantigens, B cell receptors and/or T cell receptors which are implicated in autoimmune or immunological diseases. For example, where inappropriate immune responses are raised against body tissues or environmental antigens, the immunizing compositions of the present invention may be used to induce an immune response to the autoantigens, B cell receptors and/or T cell receptors to modulate the responses and ameliorate the diseases. For example, such techniques can be efficacious in treating myasthenia gravis, lupus erythematosis, rheumatoid arthritis, multiple sclerosis, allergies and asthma.

In another aspect of the present invention, the stabilized expression plasmid system may include a polynucleotide encoding a selectable marker, or a temperature sensitive marker, such as drug resistance marker. A non-limiting example of a drug resistance marker includes aph which is known in the art to confer resistance to aminoglycosides kanamycin and/or neomycin.

The term “substantially homologous” or “substantial homologue,” in reference to a nucleotide sequence or amino acid sequence herein, indicates that the nucleic acid sequence or amino acid sequence has sufficient homology as compared to a reference sequence (e.g., a native or naturally-occurring sequence) to permit the sequence to perform the same basic function as the corresponding reference sequence; a substantially homologous sequence is typically at least about 70 percent sequentially identical as compared to the reference sequence, typically at least about 85 percent sequentially identical, preferably at least about 90 or 95 percent sequentially identical, and most preferably about 96, 97, 98 or 99 percent sequentially identical, as compared to the reference sequence. It will be appreciated that throughout the specification, where reference is made to specific nucleotide sequences and/or amino acid sequences, that such nucleotide sequences and/or amino acid sequences may be replaced by substantially homologous sequences.

C. Methods of Inducing an Immune Response

The present invention also includes methods of inducing an immune response in a subject. The immune response may be to the attenuated *S. Paratyphi* A strain itself, a selected antigen expressed by an attenuated *S. Paratyphi* A strain transformed with a stabilized expression plasmid system, or both.

In one embodiment, the method of inducing an immune response comprises administering one or more of the strains of the present invention to a subject in an amount sufficient to induce an immune response in the subject. As used herein, the strain of the present invention includes both untransformed and transformed attenuated *S. Paratyphi* A strains.

In a further embodiment, the method of inducing an immune response comprises administering a pharmaceutical formulation comprising one or more of the strains of the present invention to a subject in an amount sufficient to induce an immune response in the subject (an immunologically-effective amount).

For the sake of convenience, the strains of the present invention and pharmaceutical formulations comprising the strains are referred to herein as “immunizing compositions.” The skilled artisan will appreciate that the immunizing compositions are synonymous with vaccines.

As used herein, an “immune response” is the physiological response of the subject’s immune system to the immunizing composition. An immune response may include an innate immune response, an adaptive immune response, or both.

In a preferred embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

The subject to which the immunizing compositions may be administered is preferably a human, but may also be another mammal such as a simian, dog, cat, horse, cow or pig, or a bird, such as a chicken.

In one embodiment, the subject is a subject at risk for developing an *S. Paratyphi* A infection. In another embodiment, the subject is immunologically naïve or, alternatively, exhibits pre-existing immunity to *S. Typhi* infection or *S. Paratyphi* A infection.

In a further embodiment, the subject to which the strains of the present invention are administered develops a protective immune response against paratyphoid fever.

D. Formulations, Dosages, and Modes of Administration

The attenuated strains of the present invention, both those untransformed and transformed with a stabilized expression plasmid system, may be administered to a subject to induce an immune response. In a preferred embodiment, the strains of the present invention are administered in a pharmaceutical formulation.

The pharmaceutical formulations of the present invention may include pharmaceutically acceptable carriers, excipients, other ingredients, such as adjuvants. Pharmaceutically acceptable carriers, excipients, other ingredients are those compounds, solutions, substances or materials that are compatible with the strains of the present invention and are not unduly deleterious to the recipient thereof. In particular, carriers, excipients, other ingredients of the present invention are those useful in preparing a pharmaceutical formulation that is generally safe, non-toxic and neither biologically nor otherwise undesirable, and that may present pharmacologically favorable profiles, and includes carriers, excipients, other ingredients that are acceptable for veterinary use as well as human pharmaceutical use.

Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, more particularly: (1) Dulbecco’s phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

The mode of administration of the immunizing compositions of the present invention may be any suitable delivery means and/or methods that results in the induction of an immune response in the subject. Delivery means may include, without limitation, parenteral administration methods, such as subcutaneous (SC) injection, intravenous (IV) injection, transdermal, intramuscular (IM), intradermal (ID), as well as non-parenteral, e.g., oral, nasal, intravaginal, pulmonary (inhalation), ophthalmic, rectal administration, or by any other mode that results in the immunogenic composition contacting mucosal tissues. Preferably, administration is orally.

In one embodiment of the present invention, the immunizing compositions exists as an atomized dispersion for delivery by inhalation. Various liquid and powder formulations can be prepared by conventional methods for inhalation into the lungs of the subject to be treated. The atomized dispersion of the immunizing compositions typically contains carriers common for atomized or aerosolized dispersions, such as buffered saline and/or other compounds well known to those of skill in the art. The delivery of the immunogenic compositions via inhalation has the effect of rapidly dispersing the immunizing compositions to a large area of mucosal tissues as well as quick absorption by the blood for circulation of the immunizing compositions.

Additionally, immunizing compositions also exist in a liquid form. The liquid can be for oral dosage, for ophthalmic or nasal dosage as drops, or for use as an enema or douche. When the immunizing composition is formulated as a liquid, the liquid can be either a solution or a suspension of the immunizing composition. There are a variety of suitable formulations for the solution or suspension of the immunizing composition that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the immunizing compositions, wetting agents, sweeteners, and coloring and flavoring agents.

Delivery of the described immunizing compositions in liquid form via oral dosage exposes the mucosa of the gastrointestinal and urogenital tracts to the immunizing compositions. A suitable dose, stabilized to resist the pH extremes of the stomach, delivers the immunizing composition to all parts of the gastrointestinal tract, especially the upper portions thereof. Any methods of stabilizing the immunizing composition in a liquid oral dosage such that the effective delivery of the composition is distributed along the gastrointestinal tract are contemplated for use with the immunizing compositions described herein, including capsules and a resuspended buffer solution to protect the attenuated bacteria against the acidic pH. The particular pharmaceutically acceptable carriers or diluents employed are not critical to the present invention, and are conventional in the art. Examples of diluents include: buffers for buffering against gastric acid in the stomach, such as citrate buffer (pH 7.0) containing sucrose, bicarbonate buffer (pH 7.0) alone or bicarbonate buffer (pH 7.0) containing ascorbic acid, lactose, and optionally aspartame (Levine et al, Lancet, II:467-470 (1988)). Examples of carriers include: proteins, e.g., as found in skim milk; sugars, e.g., sucrose; or polyvinylpyrrolidone.

Delivery of the described immunizing compositions in liquid form via ophthalmic drops exposes the mucosa of the eyes and associated tissues to the immunizing compositions. A typical liquid carrier for eye drops is buffered and contains other compounds well known and easily identifiable to those of skill in the art.

Delivery of the described immunizing compositions in liquid form via nasal drops or aerosol exposes the mucosa of the nose and sinuses and associated tissues to the immunizing compositions. Liquid carriers for nasal drops are typically various forms of buffered saline.

Injectable formulations of the immunizing compositions may contain various carriers such as vegetable oils, dimethylacetamide, dimethylformamide, ethyl lactate, ethyl carbonate, isopropyl myristate, ethanol, polyols (glycerol, propylene glycol, and liquid polyethylene glycol) and the like. Physiologically acceptable excipients may include, for example, 5% dextrose, 0.9% saline, Ringer's solution or other suitable excipients. Intramuscular preparations can be dissolved and administered in a pharmaceutical excipient such as Water-for-Injection, 0.9% saline, or 5% glucose solution.

The attenuated *S. Paratyphi* A strains of the present invention may be administered to a subject in conjunction with other suitable pharmacologically or physiologically active agents, e.g., antigenic and/or other biologically active substances.

The attenuated *S. Paratyphi* A strains comprising a stabilized expression plasmid system may be administered to a subject prior to, concurrent with, or after expression of the selected antigen has begun. For example, the attenuated *S. Paratyphi* A strain comprising a stabilized expression plasmid system may be cultured for a period of time prior to administration to a subject to enable the bacterial to produce sufficient amounts of the selected antigen, such that an immune response will be raised to the selected antigen upon administration of the bacteria.

The amount and rate of administration of the immunizing compositions of the present invention may be readily determined by those of ordinary skill in the art without undue experimentation, such as by use of conventional antibody titer determination techniques and conventional bioefficacy/biocompatibility protocols. The amount and rate of administration will vary based on factors such as the weight and health of the subject, the identity of the bacteria being administered to the subject, the identity of the polypeptide being expressed in those stains engineered to express a selected antigen, the desired therapeutic effect, the desired time span of bioactivity, and the mode of administration of the immunizing composition.

In general, the amount of an immunizing composition administered to a subject is an amount sufficient to induce an immune response in the subject to a *S. Paratyphi* A strain or to the selected antigen being expressed by the *S. Paratyphi* A strain (an immunologically-effective amount). Preferably, the immune response is a protective immune response. Generally, the dosage employed will contain about $10^2$ cfu to $10^{10}$ cfu of the *S. Paratyphi* A strain, preferably about $10^2$ cfu to $10^7$ cfu, or about $10^6$ cfu to $10^9$ cfu. Formulations for oral administration comprise about $10^2$ cfu to $10^{10}$ cfu of the *S. Paratyphi* A strain, preferably about $10^6$ cfu to $10^9$ cfu, and the formulation is in a capsule or resuspended in a buffer solution to protect the attenuated bacteria against the acidic pH in the stomach. Formulations for nasal administration comprise about $10^2$ cfu to $10^{10}$ cfu of the *S. Paratyphi* A strain, preferably about $10^2$ cfu to $10^7$ cfu, and is used for intranasal administration in which the bacteria is given in drops or in aerosol.

The immunizing compositions may be administered in a single dose, or in multiple doses over prolonged periods of time. In particular, the immunizing compositions may be administered over a period of one week, two weeks, three weeks, one month, six weeks, two months, ten weeks, three months, four months, six months, one year, or for extended periods longer than one year.

The immunizing compositions may be provided in dosage unit for uniform dosage and ease of administration. Each dosage unit form contains a predetermined quantity of the strains of the present invention calculated to produce a desired immune response, in association with a pharmaceutically acceptable carrier, excipient, or other ingredient.

The present invention also includes a kit comprising one or more of the immunizing compositions of the present invention, and optionally means for administering the compositions, and instructions for administering the compositions.

E. Examples

1. Bacterial Strains and Culturing Conditions

*Escherichia coli* strain DH5 alpha was used for all plasmid constructions. Live attenuated *S. Typhi* strain CVD 908-htrA harbors deletion mutations in aroC and aroD, interrupting the aromatic compound biosynthesis pathway, and htrA, which encodes a stress response protein (see Infect Immun. 60:2 (1992), pp. 536-541 and J. Biotechnol. 44:1-3 (1996), pp. 193-196). *S. Paratyphi* A 9150 lot #11848 was purchased from the American Type Culture Collection (Manassas, Va.), and stored as CV 223 and CV 224. CV 223 was used in all experiments.

*E. coli* DH5 alpha was grown using Luria Bertani (LB) liquid medium or agar (Difco, Detroit, MI) supplemented with antibiotics carbenicillin (carb; 50 μg/ml), kanamycin (kan; 50 μg/ml) or chloramphenicol (cml; 25 μg/ml), where necessary. CVD 908-htrA and *S. Paratyphi* A 9150 and its derivatives were grown with 2× soy medium (20 g Hy-soy peptone, 10 g Hy-soy yeast extract, 3 g NaCl, ±15 g of granulated agar (Difco) per liter) with guanine (0.001% v/v) and antibiotics added where necessary. Liquid cultures were incubated at 30° C. or 37° C. at 250 rpm for 16-24 hrs unless stated otherwise.

Modified minimal medium (MMM) used for complementation analysis was composed of M9 salts (K2HPO4, 7 g/l; KH2PO4, 3 g/l; (NH4)2SO4, 1 g/l (pH7.5)), 0.5% (w/v) casamino acids (Difco), 0.5% (w/v) glucose, 0.01% (w/v) MgSO4.7H2O, 15 g of granulated agar (Difco) per liter and 1 μg/ml vitamin B1.

2. Plasmids and Molecular Genetic Techniques

Standard techniques were used for the construction of the plasmids represented here (see, for example, Sambrook et al., 1989 which is herein incorporated by reference in its entirety). Plasmid extraction and gel purification of DNA fragments were performed using QIAprep Spin Miniprep and QIAquick Gel Extraction kits, respectively, as directed by the manufacturer (Qiagen Inc., Valencia, Calif.). Plasmids pCR-Blunt II-TOPO (Invitrogen, Carlsbad, Calif.), pGEM®-T or pGEM®-T Easy (Promega, Madison, Wis.) were used as intermediates for cloning blunt ended polymerase chain reaction (PCR) products generated with Vent™ DNA Polymerase (New England Biolabs, Ipswich, Mass.). Plasmid pLowBlu 184 (E. M. Barry, unpublished data; CVD, University of Maryland, Baltimore) is a low copy number plasmid based on pACYC184 (ATCC) but containing the lactose operon sequence from pGEM®-5Zf(+) (2767-273 bp; Promega, Madison, Wis.) in place of the tetracycline resistance gene between AvaI and HindIII. Taq-Pro™ DNA Polymerase (Denville Sci., Metuchen, N.J.) was used for lambda Red-mediated mutagenesis, and for diagnostic PCR using 5 ul of a single bacterial colony diluted in 20 μl of sterile water. Taq-Pro™ DNA Polymerase was also used to add to pre-treat PCR fragments generated by Vent™ DNA Polymerase prior to cloning into pGEM®-T or pGEM®-T Easy. All restriction enzymes were purchased from New England Biolabs. T4 DNA polymerase (NEB) was used to create blunt erided DNA fragments. Electroporation of strains was performed in a Gene Pulser apparatus (Bio-Rad) set at 2.5 kV, 200Ω, and 25 μF. Molecular weight markers used in DNA gel electrophoresis are O'GeneRuler™ 1 kb DNA Ladder, ready-to-use (#SM1163, Fermentas, Hanover, Md.).

3. Lambda Red-Mediated Mutagenesis

This technique was performed as described by Datsenko and Wanner (Proc Natl Acad Sci USA. 2000 Jun. 6; 97(12): 6640-50), with certain modifications. Briefly, 10 colonies of bacteria carrying Red helper plasmid pKD46 (reader is directed to the Datsenko and Wanner reference for more information about this plasmid) were added to 20 ml of 2× soy media supplemented with carbenicillin and L-arabinose (0.2%) and grown at 30° C., 250 rpm for 3 hrs (OD 600 nm of ~0.6). Bacteria were made electrocompetent by washing 3 times with cold sterile water and concentrating 100 fold. Competent cells were electroporated with 100 ηg-1 μg of gel-purified PCR product. Following electroporation, bacteria were repaired using 2× soy medium with or without guanine. Cells were incubated in 2× soy media at 37° C. for 3 hrs prior to plating on 2× soy agar containing guanine and cml overnight. Antibiotic resistant colonies were selected and screened via PCR for alterations in the chromosomal regions of interest. Positive colonies were re-streaked onto 2× soy media containing cml, but lacking carbenicillin, to ensure loss of pKD46. Removal of the cml resistance cassette was performed as described by Datsenko and Wanner and involved using pCP20. Colonies exhibiting the desired genotype were re-streaked on 2× soy media lacking antibiotics to ensure the loss of the antibiotic resistance phenotype. Those selected for storage were re-screened via PCR prior to freezing at −70° C. in 2× soy media containing 20% (v/v) glycerol.

4. Agglutination

*S. Paratyphi* A strains were tested with commercially available sera (Difco™ *Salmonella O* Antiserum Group A, Becton Dickson, Sparks, M D, lot #4092221). Briefly, a small inoculum of bacteria taken from a fresh plate was emulsified in 20 μl of PBS on a glass slide. 5 μl of antisera was added, and the slide agitated gently until agglutination was observed. *S. flexneri* vaccine strain CVD 1208 (J Infect Dis. 2004 Nov. 15; 190(10):1745-54) or *E. coli* DH5 alpha served as negative control bacteria.

5. Assessment of Virulence by Intraperitoneal Inoculation of Mice

*Salmonella* virulence was assessed as described previously in Infect Immun. 2001 August; 69(8):4734-41. Briefly, female BALB/c mice (Charles River Breeding Laboratories, Inc., Wilmington, Mass.) aged 6 to 8 weeks (three mice per group, three groups per vaccine strain) were injected intraperitoneally (i.p.) with various 10-fold dilutions of the bacteria (grown in the presence of guanine and antibiotics where necessary, and resuspended in phosphate-buffered saline PBS) mixed with 10% (wt/vol) hog gastric mucin (Difco, lot #4092018) in a final volume of 0.5 ml. Mice were monitored for extreme moribundity (close to death) or death every 24 hr for 72 h after inoculation. The 50% lethal dose (LD50) for each group of mice was calculated by linear regression analysis.

6. Construction of a Deletion in guaBA.

The sequencing of the *S. Paratyphi* A genome was incomplete at the commencement of this project. Hence, all oligonucleotides primers and subsequent DNA templates for Lambda Red-mediated mutagenesis were constructed based on the annotated *S. Typhi* Ty2 genome sequence (Genbank accession number NC_004631, Dec. 16, 2004 version). Sequence comparison of the regions mutated in *S. Paratyphi* A with those of *S. Typhi* revealed greater than 99% DNA sequence identity.

The genes which encode inosine-5'-monophosphate dehydrogenase (guaB) and guanosine monophosphate synthetase (guaA) form an operon and are located at 414059 to 417178 bp on the *S. Typhi* Ty2 genome (SEQ ID NO: 26; see also U.S.

Pat. No. 6,190,669 for detailed information with regard to the guaBA loci). Primers CVOL 13 and CVOL 15 (Table 1) bind to sequences outside the region designated for mutation. Primers CVOL 28 and CVOL 32 were designed to bind to regions of the Lambda Red template plasmid pKD3. The resulting PCR product encoded a cml resistance cartridge flanked on either side by a 100 bp of sequence homologous to guaBA at positions 413846 to 413945 (CVOL 28) and 417109 to 417010 (CVOL 32) on the *S. Typhi* Ty2 genome, respectively.

TABLE 1

| Name | Sequence[a] | SEQ ID NO: | Target | Region[b] |
|---|---|---|---|---|
| CVOL 13 | CTGCAGTCATTCCCACTCAATGGTAGC | 4 | Ty2 | 417176-417158 |
| CVOL 15 | GGAACATCGCACAGCGCA | 5 | Ty2 | 413715-413732 |
| CVOL 26 | GTGTAGGAGCTGCTTCG | 6 | pKD3 | 31-50 |
| CVOL 27 | <u>CATATG</u>AATATCCTCCTTAG | 7 | pKD3 | 1044-1025 |
| CVOL 28 | CGAACCGTCTGGTTAAGGCGGCTTACGGTAAAAAT TGAGGAAGTTTGAGAGGATAACATGTGAGCGGGAT CAAATTCTAAATCAGCAGGTTATTCAATCGTGTAG GCTGGAGCTGCTTC | 8 | pKD3 | 31-50 |
| CVOL 32 | TTCATTGATGATGCGGTTGGAAACACGACCCAGGA AGTCATACGGCAGGTGCGCCCAGTGCGGGGTCATA AAGTCGATGGTTTCGACAGCACGCAGAGAGCATAT GAATATCCTCCTTAG | 9 | pKD3 | 1044-1025 |
| CVOL 41 | GAAGGAGTATTGCCCATGCTACGTATCG | 10 | Ty2 | 414057-414077 |
| CVOL 64 | <u>CATATG</u>AAGGAGTATTGCCCATGCT ACGTATCGCTAAAGAAG | 11 | Ty2 | 414057-414086 |
| CVOL 65 | <u>ATGCAT</u>CTGCAGTCATTCCCACTCAA TGGTAGCCGG | 12 | Ty2 | 417176-417155 |
| CVOL 85 | ACAGATAAACGCAAAGATGGCTCGGGCAAA | 13 | Ty2 | 2484865-2484836 |
| CVOL 86 | TTATTCGCCAGAAGCCTGCGCTTCCGGTTT | 14 | Ty2 | 2483597-2483626 |
| CVOL 87 | CCTGAGAATGGCATTTGCGTCGTCGTGTGC | 15 | Ty2 | 2484929-2484900 |
| CVOL 88 | ACGGCGTGTTTACAGGAAAAACGAAAGGGG | 16 | Ty2 | 2483520-2483549 |
| CVOL 89 | TCATACAGCGGAGAACGAGATAATTTGGCC | 17 | Ty2 | 2485740-2485711 |
| CVOL 90 | TTACATAAGTAAGTCACTGGGAGGCGCGCT | 18 | Ty2 | 2485027-2485056 |
| CVOL 91 | TCCATCAGGTTACAATCAGTACAGCAGATT | 19 | Ty2 | 2485800-2485771 |
| CVOL 92 | TCATTAGTATATACACAAAATCATTCGAGC | 20 | Ty2 | 2484961-2484990 |
| CVOL 122 | <u>GCGGCCGC</u>GAAGGAGAGACGGAAA TGTCATACAGCGGAGAACGAG | 21 | Ty2 | 2485752-2485722 |
| CVOL 123 | <u>TCGCGA</u>GAATTCTTACATAAGTAAG TCAGTGGGAGGCGCGCT | 22 | Ty2 | 2485024-2485056 |
| CVOL 124 | <u>GCGGCCGC</u>GAAGGAGTTTGACTCATG ACAGATAAACGCAAAGATG | 23 | Ty2 | 2484876-2484847 |
| CVOL 125 | <u>CATATG</u>TTATTCGCCAGAAGCC TGCGCTTCCGGTTT | 24 | Ty2 | 2483597-2483626 |

TABLE 1-continued

| Name | Sequence[a] | SEQ ID NO: | Target Region[b] | |
|---|---|---|---|---|
| CVOL 128 | GCGGCCGCTTACATAAGTAAGT CACTGGGAGGCGCGCT | 25 | Ty2 | 2485024-2485056 |

[a]Primers are listed in 5' > 3' direction with restriction enzyme cleavage sites underlined.
[b]Indicates region of homology to *S. Typhi* Ty2 genome (genbank accession number NC_004631) or plasmid pKD3 (genbank accession number AY048742).

Figure 2:
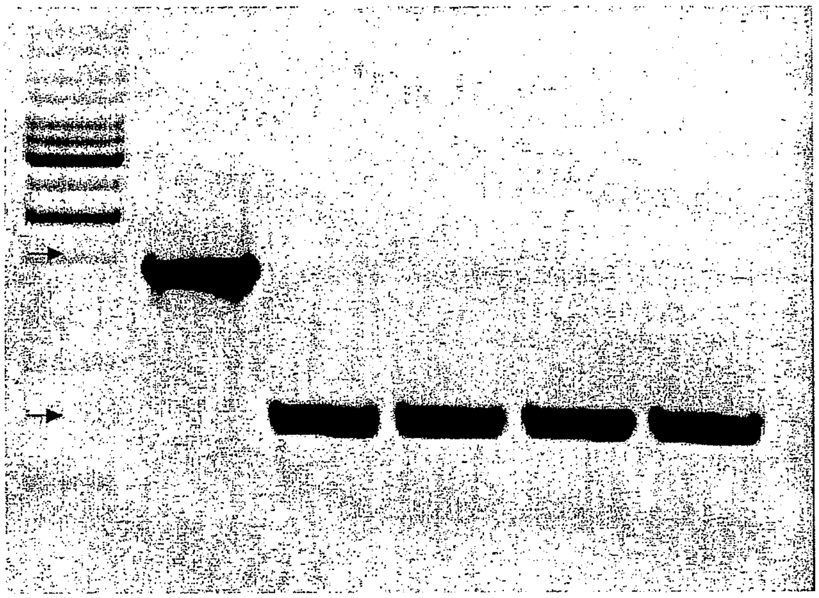
FIG. 2 shows the PCR amplification products of guaBA::cml and guaBA deletions. Lane 1 is guaBA::cml; lanes 2 to 5 are guaBA deletions. Arrows indicate molecular weight marker bands of 1.5 kb (top) and 0.5 kb (bottom).

*S. Paratyphi* A 9150 was made electrocompetent and transformed with pKD46, resulting in strain CV 250. Lambda Red mutagenesis was performed on CV 250 using the PCR product generated using primers CVOL 28 and CVOL 32 with template pKD3 containing a cml resistance marker (see the Datsenko and Wanner reference for more information about this plasmid). Transformants were plated at 37° C., and those exhibiting cml resistance were screened by PCR using CVOL 13 and CVOL 15. Unmodified guaBA amplified from *S. Paratyphi* A 9150 was found to be ~3.5 kb (FIG. 1, lane 1), whereas a ~1.4 kb fragment was found in two clones with a mutated guaBA region (FIG. 1, lanes 2 and 3). These mutants were named CV 411 and CV 412, respectively. Treatment of these mutants with pCP20 (see Datsenko and Wanner reference for more information about this plasmid) liberated the cml resistance cartridge. Four deletants were analyzed by PCR with primers CVOL 13 and CVOL 15 and found to have a ~0.5 kb band (FIG. 2, lanes 2-4) in comparison to a guaBA::cml progenitor (FIG. 2, lane 1). Resulting guaBA deletants of *S. Paratyphi* A 9150 were named CV 415-CV 418. The mutated guaBA region in CV 415 was PCR amplified with CVOL 15 and CVOL 13 and the product sequenced (polynucleotide sequence SEQ ID NO: 1); the 5' and 3' regions of SEQ ID NO: 1 are homologous to guaBA, whereas the center region is homologous to pKD3. Strain CV 415 was chosen for all subsequent studies.

7. In Vitro Complementation of the Deletion in guaBA

*S. Paratyphi* A 9150 contains an undefined auxotrophy, making it incapable of growth on minimal medium without the addition of casamino acids. ATCC strain 11511 and a CVD *S. Paratyphi* A isolate 516 are also unable to grow on minimal medium, suggesting that they contain the same auxotrophy as found in *S. Paratyphi* A 9150.

To demonstrate that Lambda Red-mediated mutagenesis only targeted guaBA in CV 415, a pLowBlu 184-based (low copy number) plasmid was designed containing a minimal fragment encoding guaBA under the control of the lactose promoter ($P_{lacZ}$). Primers CVOL 13 and CVOL 41 were used to amplify a ~3.1 kb fragment encoding guaBA with an optimized ribosome binding site (GAAGGAG) 8 bp upstream of the start codon using the chromosome of CVD 908-htrA as a template. This fragment was subcloned into pGEM®-T Easy and excised with EcoRI, blunted with T4 DNA polymerase and cloned into the NotI site of pLowBlu 184 creating pATG-guaBA (stored in CV 295).

Figure 3:
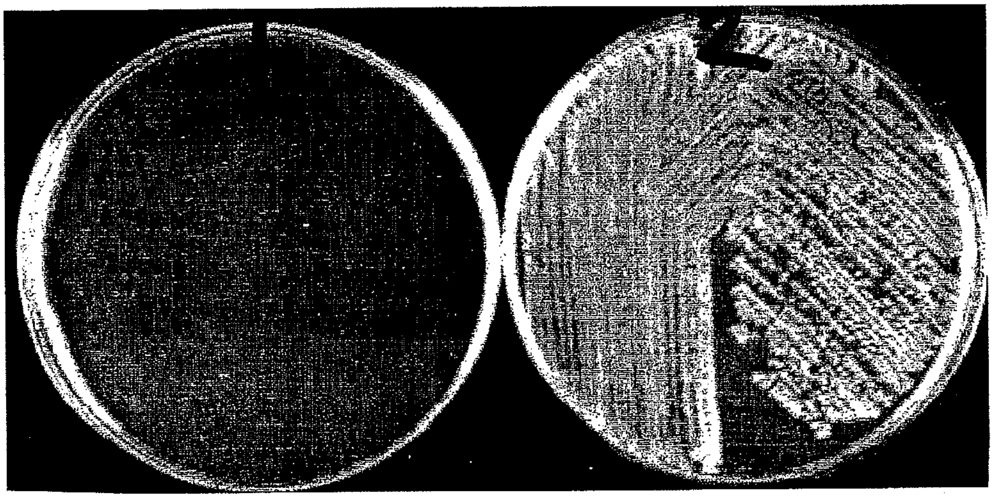
FIG. 3 shows the results of a complementation study of the guaBA deletion. Plate 1 is the guaBA mutant transformed with pLowBlu 184; plate 2 is the same mutant transformed with pATGguaBA.

CV 415 was electroporated with either pATGguaBA or pLowBlu 184 (control) and plated on 2× Soy media containing guanine and cml, creating strains CV 486 and CV 487, respectively. 2× soy medium lacking guanine is able to support the growth of guaBA deleted *S. Paratyphi* A. Single colonies of each were re-streaked onto MMM containing cml and incubated at 37° C. overnight. As shown in FIG. 3, CV 486 was able to grow on MMM (plate 2) in contrast to the control (CV 487; plate 1) indicating the minimal fragment cloned into pATGguaBA was able to complement the deletion of guaBA from the chromosome of CV 415.

8. Construction of Secondary Deletions in CV 415

In order to minimize the reversion of guaBA deleted *S. Paratyphi* A 9150 to a wild type (wt) genotype, additional genes were targeted as secondary attenuating markers. These genes were clpP and clpX, which encode a serine-protease and a chaperone ATPase, respectively (reviewed in Structure (Camb). 2004 February; 12(2):175-83). Disruption of clpP and/or clpX has been shown to significantly reduce the colonization potential of *Salmonella Typhimurium* in mice (Infect Immun. 2001 May; 69(5):3164-74). In *S. Typhi* Ty2, clpX (SEQ ID NO: 39) and clpP (SEQ ID NO: 40) are both located between 2483597 to 2485743 (SEQ ID NO: 27) on the complementary strand of the chromosome, respectively, and are expressed from individual promoters. Wt *S. Paratyphi* A 9150 was also subjected to mutagenesis such that the virulence of mutants containing single deletions in either clpX or clpP could be assessed in mice.

Figure 4:
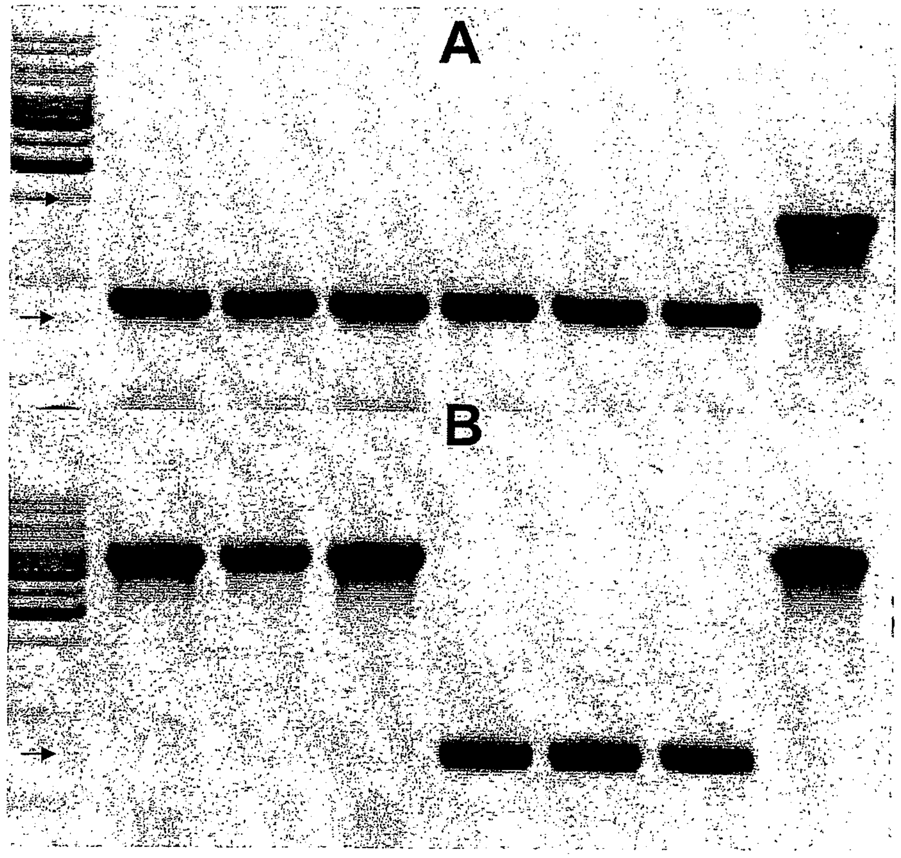
FIG. 4 shows the PCR amplification products of wt, clpX and clpX-guaBA attenuated *S. Paratyphi* A. Panel A shows PCR products produced using primers specific for clpX, whereas panel B shows PCR products produced using primers specific for guaBA. Arrows indicate molecular weight marker bands of 1.5 kb (top) and 0.5 kb (bottom) on panel A, and 3 kb (top) and 0.5 kb (bottom) on panel B.

To delete clpX, primers CVOL 85 and 86 were designed to amplify a ~1.3 kb fragment encoding clpX lacking a start codon from CVD 908-htrA. This fragment was column purified, Taq-Pro™ DNA Polymerase treated and cloned into pGEM®-T (stored in CV 472). The resulting vector, pGEM®-T::clpX was digested with NruI and EcoRI to remove a ~0.9 kb fragment, and treated with T4 DNA polymerase to create blunt ends. A cml cartridge isolated from pCR-Blunt II-TOPO as an EcoRI fragment was blunted and inserted into pGEM®-T::clpX. This cml cartridge had been previously created by PCR using CVOL 25 and CVOL 26 with pKD3 as a template (stored in CV 134). Following ligation and transformation, PCR was used with primers CVOL 26 and CVOL 85 to confirm insertion of the cml cartridge in the correct orientation for Lambda Red mutagenesis. A positive clone was identified, named pGEM®-T::(clpX::cml) and stored as CV 481.

guaBA deleted *S. Paratyphi* A (CV 415) was transformed with pKD46 and stored as CV 421. CV 421 and CV 250 (wt *S. Paratyphi* A 9150 transformed with pKD46) were subjected to Lambda Red mutagenesis with a ~1.4 kb PCR product amplified from pGEM®-T::(clpX::cml) using CVOL 85 and CVOL 86. Cml resistant mutants were isolated and screened by PCR with CVOL 87 and CVOL 88, which bind to regions outside those homologous to CVOL 85 and CVOL 86. Mutants exhibiting a correct PCR profile were selected for treatment with pCP20 to remove the cml cartridge. FIG. 4 shows that mutants containing an altered clpX gene exhibited a smaller ~0.6 kb band by PCR (Panel A, lanes 1-6) compared to that found in unaltered *S. Paratyphi* A 9150 (Panel A, lane 7). PCR analysis of the same strains with CVOL 13 and 15 confirmed that guaBA was deleted only from strains derived from CV 415 and not CV 250 (Panel B, lanes 4-6, compared to lanes 1-3 and 7). Mutants lacking clpX, and both clpX and guaBA, were stored as CV 532 and CV 534, respectively. The mutated clpX region in CV 532 and CV 534 was PCR amplified with primers CVOL 87 and CVOL 88 and the product sequenced (SEQ ID NO: 2); the 5' and 3' regions of SEQ ID NO: 2 are homologous to clpX, whereas the center region is homologous to pKD3.

To delete clpP, CVOL 89 and 90 were designed to amplify a ~0.7 kb fragment encoding clpP lacking a start codon from CVD 908-htrA. This fragment was column purified and cloned into pGEM®-T, creating pGEM®-T::clpP (stored as CV 470). pGEM®-T::clpP was digested with PstI and NsiI, T4 DNA polymerase treated and religated (creating pGEM®-T::clpPm, stored as CV 484) in order the remove NdeI and HindIII sites from the vector backbone. pGEM®-T::clpPm was then digested with NdeI and HincII to remove DNA fragments totaling ~0.5 kb in size, and T4 DNA polymerase treated. Similarly to that abovementioned, a cml cartridge isolated from pCR-Blunt II-TOPO as an EcoRI fragment was T4 DNA polymerase treated and used to replace the fragments removed from pGEM®-T::clpPm. Following ligation and transformation, PCR was used with primers CVOL 26 and CVOL 85 to confirm insertion of the cml cartridge in the correct orientation for Lambda Red mutagenesis. A positive clone was identified, named pGEM®-T::(clpPm::cml) and stored as CV 501.

Wt and guaBA deleted *S. Paratyphi* A 9150 containing pKD46 (CV 250 and CV 421, respectively) were subjected to Lambda Red mutagenesis with a ~1.4 kb PCR product amplified from pGEM®-T::(clpPm::cml) using CVOL 89 and CVOL 90. Cml resistant mutants were isolated and screened by PCR with CVOL 91 and CVOL 92, which bind to regions outside those homologous to CVOL 89 and CVOL 90. Mutants exhibiting a correct PCR profile were selected for treatment with pCP20 to remove the cml cartridge.

Figure 5:
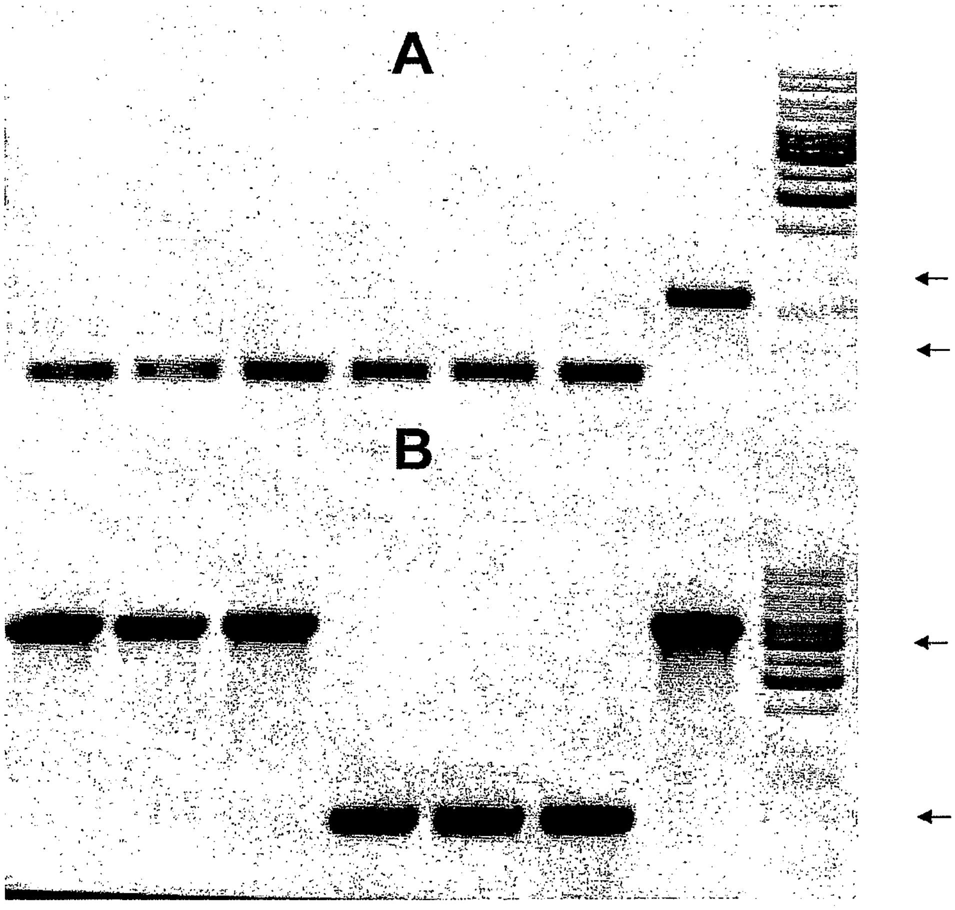
FIG. 5 shows the PCR amplification products of wt, clpP and clpP-guaBA attenuated *S. Paratyphi* A. Panel A shows PCR products produced using primers specific for clpP, whereas panel B shows PCR products produced using primers specific for guaBA. Arrows indicate molecular weight marker bands of 1 kb (top) and 0.5 kb (bottom) on panel A, and 3 kb (top) and 0.5 kb (bottom) on panel B.

FIG. 5 shows that mutants containing an altered clpP gene exhibited a smaller ~0.4 kb band by PCR (Panel A, lanes 1-6) compared to that found in unaltered *S. Paratyphi* A 9150 (Panel A, lane 7). PCR analysis of the same strains using primers CVOL 13 and 15 confirmed that guaBA was deleted only from strains derived from CV 415 and not from those based on CV 250 (Panel B, lanes 4-6, compared to lanes 1-3 and 7). Mutants lacking clpP, and both clpP and guaBA, were stored as CV 528 and CV 530, respectively. The mutated clpP region in CV 528 and CV 530 were PCR amplified with primers CVOL 87 and CVOL 88 and the product sequenced (polynucleotide sequence SEQ ID NO: 3); the 5' and 3' regions of SEQ ID NO: 3 are homologous to clpP, whereas the center region is homologous to pKD3.

9. Construction of Low Copy Plasmids for Complementation Analysis

As performed above, to confirm that the Lambda Red-mediated mutagenesis targeted only specific loci, mono- or bi-cistronic pLowBlu 184-based (low copy number) plasmids were designed containing minimal fragments encoding either clpX or clpP, or guaBA immediately downstream of either clpX or clpP. Constitutive expression of the genes in these plasmids was directed by $P_{lacZ}$.

Primers CVOL 64 and CVOL 65 were used to PCR amplify guaBA from CVD 908-htrA containing an enhanced ribosome binding site with NdeI and NsiI restriction sites at the 5' and 3' ends, respectively. The product was column purified and ligated into pCR-Blunt II-TOPQ (stored as CV 394), extracted as a ~3.5 kb NdeI-NsiI fragment and cloned into the NdeI and NsiI sites in pLowBlu 184, creating pguaBAV.2 (stored as CV 482).

To create a low copy number plasmid encoding clpP, primers CVOL 122 and CVOL 123 were used to amplify clpP with an enhanced ribosome binding site from CVD 908-htrA with NotI and NruI sites at the 5' and 3' ends, respectively. The ~0.7 kb product was column purified and ligated into pCR-Blunt II-TOPO (stored as CV 567), extracted as a NotI-NruI fragment and ligated into pLowBlu 184 previously cut with NotI and NdeI, creating pATGclpP (stored as CV 584). To construct a bi-cistronic plasmid containing clpP and guaBA, primers CVOL 122 and CVOL 128 were designed to amplify clpP with an enhanced ribosome binding site from CVD 908-htrA with Nod sites at both the 5' and 3' ends. The 0.7 kb product was column purified and ligated into pCR-Blunt II-TOPO (stored as CV 600), extracted as a NotI fragment and ligated into pguaBAV.2 previously cut with NotI, creating pATGclpPATGguaBA (stored as CV 603).

To create a low copy plasmid encoding clpX, primers CVOL 124 and CVOL 125 were used to amplify clpX with an enhanced ribosome binding site from CVD 908-htrA with NotI and NdeI sites at the 5' and 3' ends, respectively. The ~1.3 kb product was column purified and ligated into pCR-Blunt II-TOPO (stored as CV 569), extracted as a NotI-NdeI fragment and ligated into either pLowBlu 184 or pguaBAV.2 both previously cut with NotI and NdeI, creating pATGclpX (stored as CV 582) and pATGclpXATGguaBA (stored as CV 573).

10. Assessment of Virulence of *S. Paratyphi* a and Mutants in Mice $LD_{50}$ studies were performed to compare the virulence of wt *S. Paratyphi* A 9150 with that of each mutant in intraperitoneally injected mice.

Figure 6:
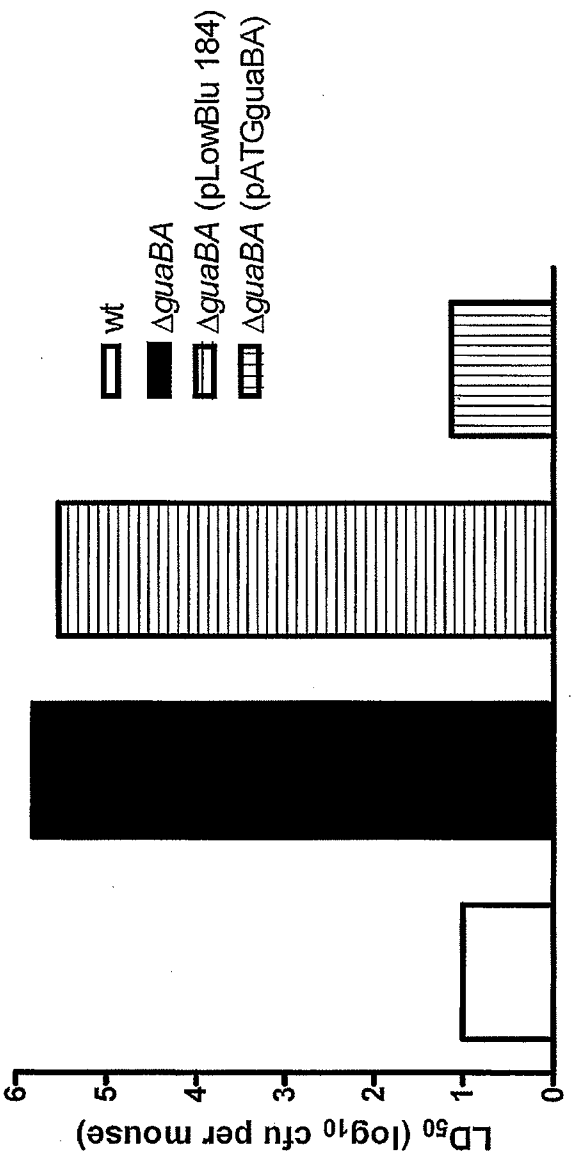
FIG. 6 is a graphical representation of data from $LD_{50}$ tests in mice injected with wt, guaBA-deleted *S. Paratyphi* A, guaBA-deleted complemented with pLowBlu 184, and guaBA-deleted complemented with pATGguaBA.

FIG. 6 shows the $LD_{50}$ data obtained with the injection of mice with wt and guaBA deleted *S. Paratyphi* A. Wt *S. Paratyphi* A has an $LD_{50}$ value of <10 bacteria per mouse. In contrast, guaBA deleted *S. Paratyphi* A had a $LD_{50}$ value ~4.5 logs greater. Complementation of the guaBA mutant with pLowBlu 184 did not alter the $LD_{50}$ value, whereas transformation with pATQguaBA restored wt-like virulence.

Figure 7:
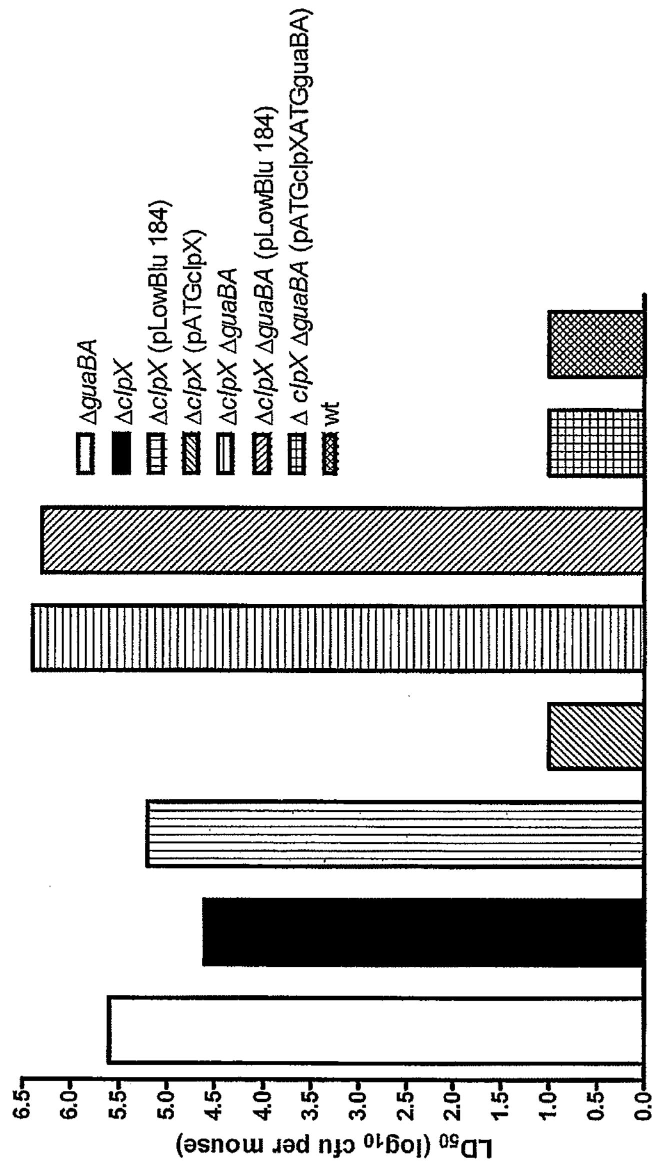
FIG. 7 is a graphical representation of data from $LD_{50}$ tests in mice injected with wt, clpX-deleted *S. Paratyphi* A, guaBA-deleted *S. Paratyphi* A, or clpX-guaBA-deleted *S. Paratyphi* A. The data include mice injected with clpX-deleted *S. Paratyphi* A complimented with pLowBlu 184 or pATGclpX, as well as clpX-guaBA-deleted *S. Paratyphi* A complimented with pLowBlu 184 or pATGclpXATGguaBA.

FIG. 7 shows the $LD_{50}$ data obtained with the injection of mice with wt *S. Paratyphi* A, clpX-deleted *S. Paratyphi* A, or clpX-guaBA-deleted *S. Paratyphi* A. The $LD_{50}$ values of wt and guaBA-deleted *S. Paratyphi* A were consistent with those achieved previously. clpX-deleted *S. Paratyphi* A displayed a ~1 log greater $LD_{50}$ value as compared to the guaBA mutants, indicating that a deletion in clpX was not as attenuating as that in guaBA. Complementation of the clpX-deleted or the clpX-guaBA deleted strains with pLowBlu 184 had no effect, whereas transformation with pATGclpX and pATGclpX-ATGguaBA, respectively, restored wt-like virulence.

Figure 8:
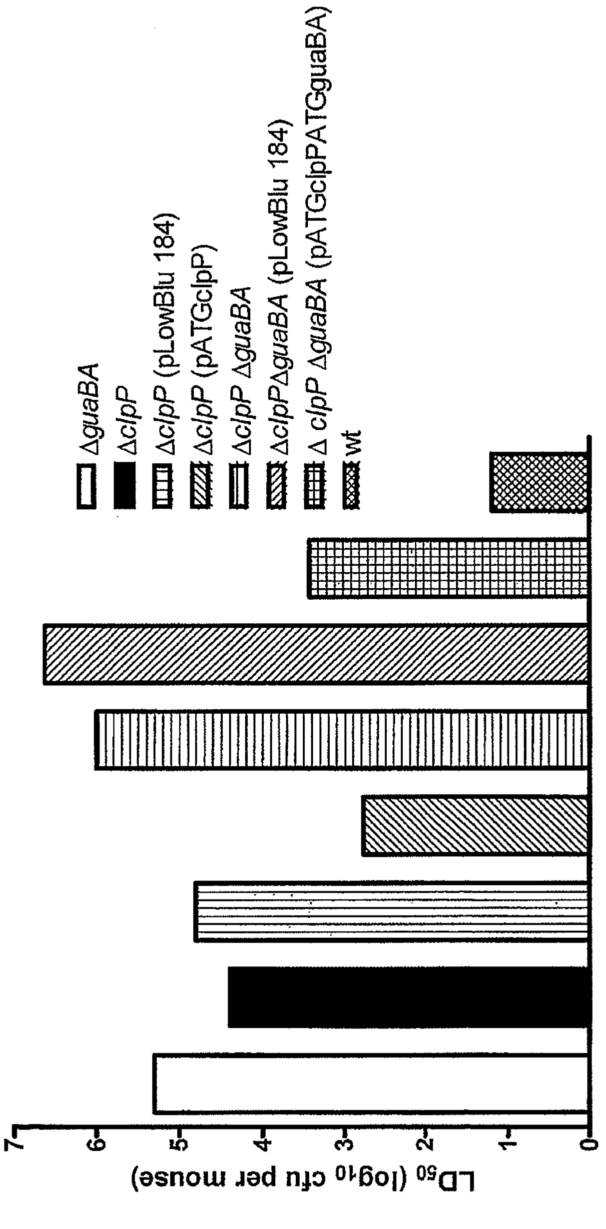
FIG. 8 is a graphical representation of data from $LD_{50}$ tests in mice injected with wt, clpP-deleted *S. Paratyphi* A, guaBA-deleted *S. Paratyphi* A, or clpP-guaBA-deleted *S. Paratyphi* A. The data include mice injected with clpP-deleted *S. Paratyphi* A complimented with pLowBlu 184 or pATGclpP, as well as clpP-guaBA-deleted *S. Paratyphi* A complimented with pLowBlu 184 or pATGclpPATGguaBA.

FIG. 8 shows the $LD_{50}$ data of mice injected with wt *S. Paratyphi* A, clpP-deleted *S. Paratyphi* A or clpP-guaBA-deleted *S. Paratyphi* A. The $LD_{50}$ values of wt and guaBA-deleted *S. Paratyphi* A were consistent to those achieved previously. As with the clpX-deleted strain, clpP-deleted *S. Paratyphi* A exhibited increased virulence as compared to the guaBA mutant. This indicated that a deletion in clpP was not as attenuating as that in guaBA. Complementation of the clpX or the clpX-guaBA-deleted strains with pLowBlu 184 had no effect on virulence. Transformation of these strains with pATGclpP and pATGclpPATGguaBA, respectively, did not completely restore wt virulence. Without being bound by any theory, regulated expression of clpP, as opposed to unregulated expression as encoded by pATGclpP and pATGclpPATGguaBA, is required to fully complement the clpP mutation.

CITED DOCUMENTS

The disclosures of the following references are incorporated herein in their entirety, as are all of the publications, patents, books, articles and other documents referred to and set forth throughout this application.

Levine M M, Herrington D, Murphy J R, Morris J G, Losonsky G, Tall B, Lindberg A, Svenson S, Baqar S, Edwards M F, Stocker B. Safety, infectivity, immunogenicity and in vivo stability of two attenuated auxotrophic mutant strains of *Salmonella Typhi,* 541Ty and 543Ty, as live oral vaccines in man. J Clin Invest 79:888-902, 1987.

Levine M M, Ferreccio C, Black R E, Chilean Typhoid Committee, Germanier R. Large-scale field trial of Ty21a live oral typhoid vaccine in enteric-coated capsule formulation. Lancet I:1049-1052, 1987.

Ferreccio C, Levine M M, Rodriguez H, Contreras R, Chilean Typhoid Committee. Comparative efficacy of two, three, or four doses of Ty21A live oral typhoid vaccine in enteric-coated capsules: a field trial in an endemic area. J Infect Dis 159:766-769, 1989.

Levine M M, Ferreccio C, Black R E, Tacket C O, Germanier R. Progress in vaccines against typhoid fever. Rev Infect Dis 2 (supplement 3):S552-S567, 1989.

Van de Verg L, Herrington D A, Murphy J R, Wasserman S S, Formal S B, Levine M M. Specific IgA secreting cells in peripheral blood following oral immunization with bivalent *Salmonella Typhi/Shigella sonnei* vaccine or infection with pathogenic *S. sonnei* in humans. Infect Immun 58:2002-2004, 1990.

Levine M M, Hone D, Heppner D G, Noriega F, Sriwathana B. Attenuated *Salmonella* as carriers for the expression of foreign antigens. Microecology and Therapy 19:23-32, 1990.

Herrington D A, Van De Verg L, Formal S B, Hale T L, Tall B D, Cryz S J, Tramont E C, Levine M M. Studies in volunteers to evaluate candidate *Shigella* vaccines: further experience with a bivalent *Salmonella Typhi-Shigella sonnet* vaccine and protection conferred by previous *Shigella sonnei* disease. Vaccine 8:353-357, 1990.

Cryz S J, Levine M M, Kaper J B. Randomized double-blind placebo-controlled trial to evaluate the safety and immunogenicity of the live oral cholera vaccine strain CVD 103-HgR in adult Swiss. Vaccine 8:577-580, 1990.

Levine M M, Ferreccio C, Cryz S, Ortiz E. Comparison of enteric-coated capsules and liquid formulation of Ty21a typhoid vaccine in a randomized controlled field trial. Lancet 336:891-894, 1990.

Servos S, Chatfield S, Hone D, Levine M M, Dimitriadis G, Pickard D, Dougan G, Fairweather N, Charles I. Molecular cloning and characterization of the aroD gene encoding 3-dehydroguinase from *Salmonella Typhi*. J Gen Micro 137:147-152, 1990.

Levine M M, Hone D, Tacket C, Ferreccio C, Cryz S. Clinical and field trials with attenuated *Salmonella Typhi* as live oral vaccines and as “carrier vaccines”. Res Microbiol 141: 807-816, 1990.

Black R E, Levine M M, Ferreccio C, Clements M L, Lanata C, Rooney J, Germanier R, and the Chilean Typhoid Committee. Efficacy of one or two doses of Ty21a *Salmonella Salmonella Typhi* vaccine in enteric-coated capsules in a controlled field trial. Vaccine 8:81-84, 1990.

Tacket C O, Losonsky G, Taylor D N, Baron L, Kopeck D, Cryz S, Levine M M. Lack of immune response to the Vi component of a Vi-positive variant of the *Salmonella Typhi* live oral vaccine strain Ty21a in volunteer studies. J Infect Dis 163:901-904, 1991.

Hone D M, Harris A M, Chatfield 5, Dougan G, Levine M M. Construction of genetically-defined double aro mutants of *Salmonella Typhi*. Vaccine 9:810-816, 1991.

Tacket C O, Hone D M, Curtiss R III, Kelly S M, Losonsky G, Guers L, Harris A M, Edelman R, Levine M M. Comparison of the safety and immunogenicity of ΔaroC ΔaroD and Δcya Δcrp *Salmonella typhi* strains in adult volunteers. Infect Immun 60:536-541, 1992.

Tacket C O, Hone D M, Losonsky G, Guers L, Edelman R, Levine M M. Clinical acceptability and immunogenicity of CVD 908 *Salmonella Typhi* vaccine strain. Vaccine 10:443-446, 1992.

Hone D M, Tacket C O, Harris A M, Kay B, Losonsky G, Levine M M. Evaluation in volunteers of a candidate live oral attenuated *Salmonella Typhi* vaccine. J Clin Invest 90:412-420, 1992.

Olanratmanee T, Levine M M, Losonsky G A, Thisyakorn U, Cryz S J Jr. Safety and immunogenicity of *Salmonella Typhi* Ty21a liquid formulation vaccine in 4- to 6-year-old Thai children. J Infect Dis 166:451-452, 1992.

Chatfield S N, Fairweather N, Charles I, Pickard D, Levine M M, Hone D, Posada M, Strugnell R A, Dougan G. Construction of a genetically defined *Salmonella Typhi* Ty2 aroA, aroC mutant for the engineering of a candidate live oral typhoid-tetanus vaccine. Vaccine 10:8-11, 1992.

Cryz S J Jr, Vanprapar N, Thisyakorn U, Olanratamanee T, Losonsky G, Levine M M, Chearskul S. Safety and immunogenicity of *Salmonella Typhi* Ty21a vaccine in young children. Infect Immun 61:1149-115, 1993.

Gonzalez C, Hone D, Noriega F, Tacket C O, Davis J R, Losonsky G, Nataro J P, Hoffman S, Malik A, Nardin E, Sztein M B, Heppner D G, Fouts T R, Isibasi A, Levine M M. *Salmonella Typhi* strain CVD 908 expressing the circumsporozoite protein of *Plasmodium falciparum*: strain construction, safety and immunogenicity. J Infect Dis 169: 927-931, 1994.

Sztein M B, Wasserman S S, Tacket C O, Edelman R, Hone D, Lindberg A A, Levine M M. Cytokine production patterns and lymphoproliferative responses in volunteers orally immunized with attenuated vaccine strains of *Salmonella Typhi*. J Infect Dis 170:1508-1517, 1994.

Hone D M, Harris A M, Lim V, Levine M M. Construction and characterization of isogenic O-antigen variants of *Salmonella Typhi*. Molec Microbiol 13:525-530, 1994.

Pickard D, Li J, Roberts M, Maskell D, Hone D, Levine M, Dougan G, Chatfield S. Characterization of defined ompR mutants of *Salmonella Typhi*: ompR is involved in the regulation of Vi polysaccharide expression. Infect Immun 62:3984-3993, 1994.

Noriega F R, Wang J Y, Losonsky G, Maneval D R, Hone D M, Levine M M. Construction and characterization of attenuated ΔaroA ΔvirG *Shigella flexneri* 2a strain CVD 1203, a prototype live oral vaccine. Infect Immun 62:5168-5172, 1995.

Gómez-Duarte, O G, Galen J, Chatfield S N, Rappuoli R, Eidels L, Levine M M. Expression of fragment C of tetanus toxin fused to a carboxyl-terminal fragment of diphtheria toxin in *Salmonella Typhi* CVD 908 vaccine strain. Vaccine 13:1596-1602, 1995.

Cryz S J Jr, Que J U, Levine M M, Wiedermann G, Kollaritsch H. Safety and immunogenicity of a live oral bivalent typhoid fever (*Salmonella Typhi*-Ty21a) cholera (*Vibrio cholerae* CVD 103-HgR) vaccine in healthy adults. Infect Immun 63:1336-1339, 1995.

Sztein M B, Tanner M K, Polotsky Y, Orenstein J M, Levine M M. Cytotoxic T lymphocytes after oral immunization with attenuated strains of *Salmonella Typhi* in humans. J Immunol 155:3987-3993, 1995.

Levine M M, Galen J, Barry E, Noriega F, Chatfield S, Dougan G, Tacket C. Attenuated *Salmonella* as live oral vaccines against typhoid fever and as live vectors. J Biotechnology 44:193-196, 1995.

Noriega F R, Losonsky G, Wang J Y, Formal S B, Levine M M. Further characterization of ΔaroA, ΔvirG *Shigella flexneri* 2a strain CVD 1203 as a mucosal *Shigella* vaccine and as a live vector for delivering antigens of enterotoxigenic *Escherichia coli*. Infect Immun 64:23-27, 1996.

Noriega F R, Losonsky G, Lauderebaugh C, Liao F M, Wang J Y, Levine M M. Engineered ΔguaBA ΔvirG *Shigella flexneri* 2a strain CVD 1205: construction, safety, immunogenicity, and potential efficacy as a mucosal vaccine. Infect Immun 64:3055-3061, 1996.

Kotloff K, Noriega F, Losonsky G, Sztein M B, Nataro J P, Levine M M. Safety, immunogenicity and transmissibility in humans of CVD 1203, a live oral *Shigella flexneri* 2a vaccine candidate attenuated by deletions in aroA and virG. Infect Immun 64:4542-4548, 1996.

Barry E M, Gomez-Duarte O, Chatfield S, Rappuoli R, Losonsky G A, Galen J E, Levine M M. Expression and immunogenicity of pertussis toxin S1 subunit-tetanus toxin fragment C fusions in *Salmonella Typhi* vaccine strain CVD 908. Infect Immun 64:4172-4181, 1996.

Tacket C O, Sztein M B, Losonsky G A, Wasserman S S, Nataro J P, Edelman R, Galen J E, Pickard D, Dougan G, Chatfield S N, Levine M M. Safety of live oral *Salmonella Typhi* vaccine strains with deletions in htrA and aroC aroD and immune response in humans. Infect Immun 65:452-456, 1997.

Levine M M, Galen J, Barry E, Noriega F, Tacket C, Sztein M, Chatfield S, Dougan G, Losonsky G, Kotloff K. Attenuated *Salmonella Typhi* and *Shigella* as live oral vaccines and as live vectors. Behring Inst Mitt 98:120-123, 1997.

Tacket C O, Kelly S M, Schodel F, Losonsky G, Nataro J P, Edelman R, Levine M M, Curtiss R III. Safety and immunogenicity in humans of an attenuated *Salmonella Typhi* vaccine vector strain expressing plasmid-encoded hepatitis B antigens stabilized by the Asd-balanced lethal system. Infect Immun 65:3381-3385, 1997.

González C R, Noriega F R, Huerta S, Santiago A, Vega M, Paniagua J, Ortiz-Navarrete V, Isibasi A, Levine M M. Immunogenicity of a *Salmonella Typhi* CVD 908 candidate vaccine strain expressing the major surface protein gp63 of *Leishmania mexicana mexicana*. Vaccine 16:9/10 1043-1052, 1998.

Orr N, Galen J E, Levine M M. Expression and immunogenicity of a mutant diphtheria toxin molecule, CRM197, and its fragments in *Salmonella Typhi* vaccine strain CVD 908-htrA. Infect Immun 67:4290-4294, 1999.

Levine M M, Ferreccio C, Abrego P, San Martin O, Ortiz E, Cryz S C. Duration of efficacy of Ty21a, attenuated *Salmonella Typhi* live oral vaccine. Vaccine 17:2 Supplement S22-S27, 1999.

Pasetti M F, Anderson R J, Noriega F R, Levine M M, Sztein M B. Attenuated ΔguaBA *Salmonella Typhi* vaccine strain CVD 915 as a live vector utilizing prokaryotic or eukaryotic expression systems to deliver foreign antigens and elicit immune responses. Clin Immun 92:76-89, 1999.

Galen J E, Nair J, Wang J Y, Tanner M K, Sztein M B, Levine M M. Optimization of plasmid maintenance in the attenuated live vector vaccine *Salmonella Typhi* strain CVD 908-htrA. Infect Immun 67:6424-6433, 1999.

Kotloff K L, Noriega F R, Samandari T, Sztein M B, Losonsky G A, Nataro J P, Picking W D, Levine M M. *Shigella flexneri* 2a strain CVD 1207 with specific deletions in virG, sen, set and guaBA is highly attenuated in humans. Infect Immun 68:1034-39, 2000.

Tacket C O, Sztein M B, Wasserman S S, Losonsky G, Kotloff K L, Wyant T L, Nataro J P, Edelman R, Perry J, Bedford P, Brown D, Chatfield S, Dougan G, Levine MM. Phase 2 clinical trial of attenuated *Salmonella enterica serovar Typhi* oral live vector vaccine CVD 908-htrA in U.S. volunteers. Infect Immun 68:1196-1201, 2000.

Anderson R J, Pasetti M F, Sztein M B, Levine M M, Noriega F R. ΔguaBA attenuated *Shigella flexneri* 2a strain CVD 1204 as a *Shigella* vaccine and as a live mucosal delivery system for fragment C of tetanus toxin. Vaccine 18:2193-2202, 2000.

Tacket C O, Galen J, Sztein M B, Losonsky G, Wyant T L, Nataro J, Wasserman S S, Edelman R, Chatfield S, Dougan G, Levine M M. Safety and immune responses to attenuated *Salmonella enterica serovar Typhi* oral live vector vaccines expressing tetanus toxin fragment C. Clin Immunol 97:146-153, 2000.

Pasetti M F, Tanner M K, Pickett T E, Levine M M, Sztein M. Mechanisms and cellular events associated with the priming of mucosal and systemic immune responses to *Salmonella enterica serovar Typhi* live vector vaccines delivered intranasally in the murine model. Vaccine 18:3208-3213, 2000.

Wu S, Beier M, Sztein M, Galen J E, Pickett T, Holder A A, Gómez-Duarte O, Levine M M. Construction and immunogenicity in mice of attenuated *Salmonella Typhi* expressing *Plasmodium falciparum* merozoite surface protein (MSP-1) fused to tetanus toxin fragment C. J. Biotechnol. 83:125-135, 2000.

Wang J Y, Noriega F R, Galen J E, Barry E, Levine M M. Constitutive expression of the Vi polysaccharide capsular antigen in attenuated *Salmonella enterica serovar Typhi* oral vaccine strain CVD 909. Infect Immun 68:4647-4652, 2000.

Koprowski H II, Levine M M, Anderson R A, Losonsky G, Pizza M, Barry E M. Attenuated *Shigella flexneri* 2a vaccine strain CVD 1204 expressing colonization factor antigen I and mutant heat-labile enterotoxin of enterotoxigenic *Escherichia coli*. Infect Immun 68:4884-92, 2000.

Gómez-Duarte O, Pasetti M, Santiago A, Sztein M B, Hoffman S L, Levine M M. Expression, secretion and immunogenicity of the *Plasmodium falciparum* SSP-2 protein in *Salmonella* vaccine strains by a type I secretion system. Infect Immun 69:1192-1198, 2001.

Orr N, Galen J E, Levine M M. Novel use of anaerobically induced promoter, dmsA, for controlled expression of Fragment C of tetanus toxin in live attenuated *Salmonella enterica serovar Typhi* strain CVD 908-htrA. Vaccine 19:1694-1700, 2001.

Altboum Z, Barry E M, Losonsky G, Galen J E, Levine M M. Attenuated *Shigella flexneri* 2a ΔguaBA strain CVD 1204 expressing ETEC CS2 and CS3 fimbriae as a live mucosal vaccine against *Shigella* and enterotoxigenic *Escherichia coli* infection. Infect Immun 69:3150-8, 2001.

Wang J Y, Pasetti M F, Noriega F R, Anderson R S, Wasserman S S, Galen J E, Sztein M B, Levine M M. Construction, genotypic and phenotypic characterization, and immunogenicity of attenuated ΔguaBA *Salmonella enterica serovar Typhi* strain CVD 915. Infect Immun 69:4734-4741, 2001.

Galen J E, Levine M M. Can a "flawless" live vector vaccine strain be engineered? Trends Microbiol 9:372-376, 2001.

Kotloff K L, Taylor D N, Sztein M B, Wasserman S S, Losonsky G A, Nataro J P, Venkatesan M, Hartman A, Picking W D, Katz D E, Campbell J D, Levine M M, Hale T L. Phase I evaluation of ΔvirG *Shigella sonnei* live, attenuated, oral vaccine strain WRSS1 in healthy adults. Infect Immun 70:2016-21, 2002.

Pasetti, M, Levine M M, Sztein M B. Animal models paving the way for clinical trials of attenuated *Salmonella enterica serovar Typhi* live oral vaccines and live vectors. Vaccine. 21:401-18, 2003.

Pasetti M F, Barry E M, Losonsky G, Singh M, Medina-Moreno S M, Polo J M, Robinson H, Sztein M B, Levine M M. Attenuated *Salmonella enterica serovar Typhi* and *Shigella flexneri* 2a strains mucosally deliver DNA vaccines encoding measles virus hemagglutinin, inducing specific immune responses and protection in cotton rats. J Virol 77:5209-5217, 2003.

Salerno-Goncalves R, Wyant T L, Pasetti M F, Fernandez-Vina M, Tacket C O, Levine M M, Sztein M B. Concomitant Induction of CD4(+) and CD8(+) T Cell Responses in Volunteers Immunized with *Salmonella enterica* Serovar Typhi Strain CVD 908-htrA. J Immol. 170:2734-2741, 2003.

Tacket C O, Pasetti M F, Sztein, M B, Livio S, Levine M M. Immune responses to an oral Typhoid vaccine strain modified to constitutively express Vi capsular polysaccharide. J Infect Dis, 190:565-570, 2004.

Vindurampulle C J, Cuberos L F, Barry E M, Pasetti M F, Levine M M. Recombinant *Salmonella enterica serovar Typhi* in a prime-boost strategy. Vaccine 22(27-28):3744-3750, 2004.

Capozzo A V, Cuberos L, Levine M M, Pasetti M F. Mucosally delivered *Salmonella* live vector vaccines elicit potent immune responses against a foreign antigen in neonatal mice born to naive and immune mothers. Infect Immun 72:4637-4646, 2004.

Kotloff K L, Pasetti M F, Barry E M, Nataro J P, Wasserman S S, Sztein M B, Picking W D, Levine M M. Deletion in the *Shigella* enterotoxin genes further attenuates *Shigella flexneri* 2a bearing guanine auxotrophy in a Phase 1 trial of CVD 1204 and CVD 1208. J Infect Dis 190:1745-1754, 2004.

Galen J E, Zhao L, Chinchilla M, Wang J Y, Pasetti M F, Green J, Levine M M. Adaptation of the endogenous *Salmonella enterica serovar Typhi* clyA-encoded hemolysin for antigen export enhances the immunogenicity of anthrax protective antigen domain 4 expressed by the attenuated live vector vaccine strain CVD 908-htrA. Infect Immun 72:7096-7106, 2004.

What is claimed is:

1. An attenuated *Salmonella Paratyphi* A strain, wherein said strain has a deletion mutation in the guaBA locus, and a deletion mutation in the clpX gene, wherein said deletion mutation in the guaBA locus is a deletion mutation in the guaB gene, a deletion mutation in the guaA gene, or a deletion mutation in both guaB and guaA genes.

2. The attenuated *Salmonella Paratyphi* A strain of claim 1, wherein said strain further comprises a deletion mutation in the clpP gene.

3. The attenuated *Salmonella Paratyphi* A strain of claim 1, wherein said strain is a mutant of the *S. Paratyphi* A 9150 strain.

4. A pharmaceutical formulation comprising attenuated *Salmonella Paratyphi* A strain of claim 1 and a pharmaceutically acceptable carrier.

5. The pharmaceutical formulation of claim 4, wherein said formulation is an oral pharmaceutical formulation.

6. A method of inducing an immune response in a subject to an attenuated *Salmonella Paratyphi* A strain, comprising administering an immunologically-effective amount of the pharmaceutical formulation of claim 4 to a subject.

* * * * *

UNITED STATES PATENT AND TRADEMARK OFFICE

CERTIFICATE OF CORRECTION

PATENT NO. : 8,475,810 B2
APPLICATION NO. : 12/091929
DATED : July 2, 2013
INVENTOR(S) : Christofer Vindurampulle It is certified that error appears in the above-identified patent and that said Letters Patent is hereby corrected as shown below:

In the Specification:

Column 1, at line 4, insert:

--STATEMENT REGARDING FEDERALLY SPONSORED RESEARCH

This invention was made with government support under Grant Number AI029471 awarded by the National Institutes of Health. The government has certain rights in the invention.--

Signed and Sealed this
Third Day of September, 2013

Teresa Stanek Rea
*Acting Director of the United States Patent and Trademark Office*